United States Patent
Andre et al.

(10) Patent No.: US 11,503,837 B2
(45) Date of Patent: Nov. 22, 2022

(54) METHODS FOR OPTIMISING METABOLITE PRODUCTION IN GENETICALLY MODIFIED PLANTS AND FOR PROCESSING THESE PLANTS

(71) Applicant: BASF PLANT SCIENCE COMPANY GMBH, Ludwigshafen (DE)

(72) Inventors: Carl Andre, Research Triangle Park, NC (US); Anthony J. Cavender, Ames, IA (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 578 days.

(21) Appl. No.: 16/300,358

(22) PCT Filed: May 12, 2017

(86) PCT No.: PCT/EP2017/061427
§ 371 (c)(1),
(2) Date: Nov. 9, 2018

(87) PCT Pub. No.: WO2017/194728
PCT Pub. Date: Nov. 16, 2017

(65) Prior Publication Data
US 2019/0141895 A1 May 16, 2019

(30) Foreign Application Priority Data
May 12, 2016 (EP) .................................... 16169443

(51) Int. Cl.
*A23D 9/02* (2006.01)
*C12N 15/82* (2006.01)
*A01D 45/30* (2006.01)

(52) U.S. Cl.
CPC ............ *A23D 9/02* (2013.01); *C12N 15/8247* (2013.01); *A01D 45/30* (2013.01)

(58) Field of Classification Search
CPC ............................. C12N 15/8247; A23D 9/02
See application file for complete search history.

(56) References Cited

U.S. PATENT DOCUMENTS

| | | |
|---|---|---|
| 5,411,561 A | 5/1995 | Conley |
| 5,884,225 A | 3/1999 | Allen et al. |
| 7,047,690 B2 | 5/2006 | Moser et al. |
| 2012/0016144 A1* | 1/2012 | Petrie ............... A61P 25/14 554/9 |
| 2013/0338387 A1* | 12/2013 | Petrie ............... A61P 1/04 554/224 |

FOREIGN PATENT DOCUMENTS

| | | |
|---|---|---|
| CA | 2196940 A1 | 8/1998 |
| WO | WO-2005/103253 A1 | 11/2005 |
| WO | WO-2007/096387 A1 | 8/2007 |
| WO | WO-2016/075326 A2 | 5/2016 |

OTHER PUBLICATIONS

Sintim et al (Evaluating Agronomic Responses of Camelina to Seeding Date under Rain-Fed Conditions. Agronomy Journal, 108:349-357, Jan. 2016) (Year: 2016).*
Aksouh-Harradj et al (Canola response to high and moderately high temperature stresses during seed maturation. Can. J. Plant Sci. 967-980, 2006) (Year: 2006).*
Napier et al (Transgenic plants as a sustainable, terrestrial source of fish oils. Eur. J. Lipid Sci. Technol. 117, 1317-1324, 2015) (Year: 2015).*
Gan et al (Assessment of seed shattering resistance and yield loss in five oilseed crops. Can J plant Sci. 267-270, 2008). (Year: 2008).*
Baux et al., "Effects of minimal temperatures on low-linolenic rapeseed oil fatty-acid composition", European Journal of Agronomy, vol. 29, Issues 2-3, Aug. 2008, pp. 102-107.
Deng et al., "Temperature effects on fatty acid composition during development of lowlinolenic oilseed rape (Brassica napus L.)",Journal of the American Oil Chemists' Society, vol. 75, Issue 7, Jul. 1998, pp. 759-766.
Dwyer et al., "A General Thermal Index for Maize", Agronomy Journal Abstract—Grain and Oil Crops, vol. 91, Issue 6, 1999, pp. 940-946.
Dwyer et al., "Guidelines for Comparisons among Different Maize Maturity Rating Systems", Agronomy Journal Abstract—Grain and Oil Crops, vol. 91, Issue 6, 1999, pp. 946-949.
European Search Report for EP Patent Application No. 16169443.5, dated Nov. 28, 2016, 4 pages.
Fowler et al., "Lipid and Morphological Changes in Developing Rapeseed, *Brassica napus*", Canadian Journal of Plant Science, vol. 50, Issue 3, 1970, pp. 233-247.
Haslam et al., "The Modification of Plant Oil Composition Via Metabolic Engineering—Better Nutrition by Design", Plant Biotechnology Journal, vol. 11, Issue 2, Feb. 2013, pp. 157-168.
International Search Report for PCT Patent Application No. PCT/EP2017/061427, dated Aug. 29, 2017, 6 pages.
Jeh et al, "Lipid body formation by Thraustochytrium aureum (ATCC 34304) in response to cell age", Korean Journal of Chemical Engineering, vol. 25, Issue 5, Sep. 2008, pp. 1103-1109.
Khan et al., "Changes in Fatty Acid Content and Composition in Silage Maize During Grain Filling", Journal of Science of Food and Agriculture, vol. 91, Issue 6, 2011, pp. 1041-1049.
Miller et al., "Using Growing Degree Days to Predict Plant Stages", Montana State University, Montguide, Jul. 2001, pp. 1-7.

(Continued)

*Primary Examiner* — Bratislav Stankovic
*Assistant Examiner* — Wayne Zhong
(74) *Attorney, Agent, or Firm* — Marshall, Gerstein & Borun LLP

(57) ABSTRACT

The present invention relates to the field of producing particular metabolites of interest by engineered crop plants such as transgenic crop plants. Provided are methods that are easily applicable by farmers to determine when the metabolites of interest hake reached an optimal content in the plant. These methods also help to facilitate decisions about the timeframe for preparing harvest or harvesting the engineered crop plant.

11 Claims, 7 Drawing Sheets

(56) References Cited

OTHER PUBLICATIONS

Pavlista et al., "Planting date and development of spring-seeded irrigated canola, brown mustard and camelina", Industrial Crops and Products, vol. 33, Issue 2, Mar. 2011, pp. 451-456.
Schulte et al., "Increased growing temperature reduces content of polyunsaturated fatty acids in four oilseed crops", Industrial Crops and Products, vol. 51, Nov. 2013, pp. 212-219.
Vera et al., "Yield and quality of canola seed as affected by stage of maturity at swathing", Canadian Journal of Plant Science, vol. 87, Issue 1, 2007, pp. 13-26.

* cited by examiner

METHODS FOR OPTIMISING METABOLITE PRODUCTION IN GENETICALLY MODIFIED PLANTS AND FOR PROCESSING THESE PLANTS

This application is a National Stage application of International Application No. PCT/EP2017/061427, filed May 12, 2017, which claims the benefit of European Patent Application No. 16169443.5, filed on May 12, 2016.

BACKGROUND

Polyunsaturated fatty acids, and in particular omega-3 fatty acids attracted much attention because of their potential health benefits compared to saturated fatty acids. High levels of polyunsaturated fatty acids (PUFAs) are found in the oil of walnuts, canola, sunflower and sesame. Some omega-3 fatty acids belong to the group of very long chain polyunsaturated fatty acids (VLCPUFAs) that have aliphatic tails of 20 carbons and more. They play an important role in human metabolism as parts of membrane phospholipids and as precursors for eicosanoids and docosanoids. In particular docosahexaenoic acid (DHA, 22:6-Δ4,7,10,13,16,19) and eicosapentaenoic acid (EPA, 20:5-Δ5,8,11,14,17) gained much interest (Swanson et al., Adv Nutr 3:1-7, 2012) because the efficiency at which humans can synthesise EPA and DHA from alpha-linolenic acid is very low (below 5%) and supplementary dietary intake of EPA and DHA is necessary. Dietary sources of EPA and DHA (and of VLCPUFAs in general) are limited: these fatty acids are synthesized mainly by marine algae and subsequently taken up by fish feeding on the algae. However, fish is not a sustainable source for supplying EPA and DHA to humans.

Brassica napus or rapeseed is one of the largest sources of vegetable oil in the world, its oil comprises typically 57-63% Oleic acid (18:1 (n-9)), 18-25% Linoleic acid (18:2 (n-6)) and 8-13% Linolenic acid (18:3 (n-6) or 18:3 (n-3)), all having an aliphatic tail of 18 carbons. Recently Brassica napus was genetically engineered to produce two VLCPUFAs, Eicosapentaenoic acid (EPA) and Docosahexaenoic acid (DHA), in seeds (WO05103253 & PCT/EP2015/076631). Seeds from these plants reportedly have increased levels of EPA and DHA and could be a valuable replacement for fish oil as a source of EPA and DHA.

As Brassica is an indeterminate plant, at any given time post flowering there will be seeds of various maturity and oil content on the plant. The variable maturation stage of the seeds creates two problems: chlorophyll presence in the least mature seeds, which lowers oil quality, and the variable age of siliques on the plant may cause seed loss if harvest is delayed too long as the older siliques will begin to shatter. In the United States, North Dakota is where the bulk of oil seed rape is grown (approximately 90%) and the crop is typically harvested by means of swathing (the process of cutting the crop and laying the cut stems with attached seed pods in rows in the field). Swathing encourages the youngest of the seeds to ripen in the field, which lowers chlorophyll and moisture content. Based on various maturity parameters, such as plant coloration, seed pigment content, and access to the crop/field conditions, the crop is swathed and then combined. A typical crop is considered mature and ready for swathing when 60% of the seeds have changed color from green to dark brown. With respect to plant maturation, growing degree days (GDD) is the best forecasting tool to predict when the crop will be ready for harvest. Plant maturation is dependent upon time and temperature, in particular time spent within a certain temperature threshold (too cold or too hot temperatures are both detrimental and can cause stunting of growth).

An example of growing degree days and corresponding crop development has been published by the Montana State University Extension Service (Miller et al. 2001 Montana State University. MT200103 AG 7/2001). For Brassica napus flowering begins at 1079-1230 GDD° F. (GDD calculated with ° F.), seed fill begins at 1781-1965 GDD° F., maturity occurs at 2418-2633 GDD° F., and swathing is recommended at 2609-2834 GDD° F. All of these GDD are measured from the time of sowing, but GDD can be calculated between any dates for which weather data is available, for example, from flowering to swathing. GDD is an effective indicator of crop maturity, and as such, methods have been developed to use pre-determined GDD values to guide the production and harvest of green cicer beans (U.S. Pat. No. 7,047,690) and raisins (U.S. Pat. No. 5,411,561).

The impact of harvest timing/seed maturation and fatty acid profile and/or seed oil accumulation has been examined in brassica plants (Baux et al. 2008 Europ. J. Agronomy 29:102-107). The authors observed that higher temperatures during seed filling led to higher mono-unsaturated fatty acid content, and speculate that this observation could be due to temperature optima for the desaturases involved in fatty acid biosynthesis, though no data are shown to support this hypothesis. Work on maize stover and kernel fatty acid accumulation found different kinetics of fatty acid accumulation depending upon genotype and tissue sampled (Khan et al. 2011 J. Sci Food Agri. 91, 1041-1049). The stover displayed a trend wherein during the period of grain filling the contents of C16:0, C18:2 and C18:3 and total fatty acids declined while the levels of C18:0 and C18:1 increased. In whole ears, the levels of C16:0, C18:1, C18:2 increased during grain fill. At full maturity the content of polyunsaturated fatty acids in both stover and ears did not differ among the six genotypes examined. These data suggest that the degree of maturity may have a more powerful impact than genetic background on kernel fatty acid profile. Work examining the impact of growing temperature on PUFA levels in several oil seed crops showed that the molar percentage of oleic, linoleic and linolenic acids of soybean, canola, and sunflower depend on the temperature during grain fill, with higher temperatures being detrimental to the accumulation of PUFAs, while enhancing the accumulation of mono-unsaturated fatty acids (Schulte et al. 2013 Industrial Crops and Products 51:212-219). This would suggest that increased growing degree days would not be beneficial to overall PUFA levels. In field grown brown mustard (Brassica juncea cv. Arid) camelina (Camelina sativa cv. Boa) and canola (Brassica napus cv. Hyola 401), planting time influences the level of C18:1, with an increase corresponding to a later planting date (Pavlista et al. 2011 Industrial Crops Products 33:451-456). At the same time only camelina demonstrated an increase in C18:2 and of C20:1 and C18:3 due to late planting. This series of observations supports the hypothesis that fatty acid profile in a given part of the plant might be altered by controlling the sowing time or harvesting time, but does not provide significant insight into what one might expect to see in a plant that synthesizes fatty acids that are not normally present in the plant.

Degree of maturity has an impact on the fatty acid profile of organisms that naturally produce the PUFAs DHA and EPA (Jeh et al 2008 Korean J Chem. Engineering 25:1103-1109). For the microalga Thraustochytrium aureum (ATCC 34304), as the cells age, fatty acid production declines significantly and overall stored fatty acid levels, and PUFAS in particular, decrease, and storage lipid body size is reduced. This data would suggest that in an organism that naturally produces EPA and DHA one would expect the proportion of these fatty acids to go down over time after an initial peak in accumulation.

In surveying the accumulation profile of various fatty acids over seed and plant development, the above studies indicate that fatty acid profile in the plant can change over the course of maturation. A priori one could not predict, based on the current state of the art, how delaying or expediting harvest or other processing of the plants would influence the levels of certain metabolites (like fatty acids) that are not native to the plant because their pattern of synthesis seems to be species specific and difficult to discern for an artificial system, such as, for example, the accumulation of significant amounts of DHA and EPA in *Brassica napus*.

DETAILED DESCRIPTION

The concentration of a metabolite of interest in plant samples is usually determined in a laboratory with sophisticated equipment. Farmers however rarely have access to such diagnostic tools and have little or no guidance for monitoring the synthesis and accumulation of a metabolite of interest amongst all other metabolites in plants growing in the field. In addition, and importantly to note, transgenic plants producing a non-endogenous metabolite of interest (i.e., a metabolite of interest that is not produced by the non-engineered plant or non-transgenic plant) will synthesise this metabolite of interest depending on the type and expression pattern of the transgenes involved in the synthesis pathway. Therefore the accumulation of a metabolite of interest will follow a particular pattern that is not linked to the synthesis pattern of other (related) metabolites. Another consequence is that one cannot rely on accumulation patterns in plant species that naturally produce the metabolite of interest. Other factors that influence the accumulation pattern are the intrinsic stability of the metabolite of interest, or the possibility that the metabolite of interest can be further converted to other metabolites at certain developmental stages of the plant or in specific plant parts. This situation can be extrapolated to any plant in which the synthesis of a metabolite of interest is altered through genetic modification of the plant (like genetic engineering, genome editing, mutagenesis etc.). Therefore it is difficult for a farmer to determine a suitable growth stage at which the metabolite of interest has reached an optimal concentration, or to determine a suitable point in time for harvesting the plants producing the metabolite of interest.

The present invention now provides a methodology to link the particular accumulation pattern of a metabolite of interest in an engineered plant as determined in a laboratory to easily discriminable plant growth properties or to parameters derived from plant growth properties. In a specific embodiment, the optimal content of a metabolite of interest is determined in view of the harvest of the plants. This method allows defining a suitable harvesting time of plants when the metabolite of interest has reached a desired concentration in the harvestable parts of the plants. The invention thus provides a method for determining a growth stage or other plant property at which the optimal content of a metabolite of interest is reached for harvesting an engineered plant or a part thereof, wherein the synthesis of the metabolite of interest is modulated through a genetic modification, and which method comprises (i) cultivating the engineered plant and making a correlation between an accumulation pattern of the metabolite of interest and the plant growth stage or other plant property, (ii) determining the point in time at which the optimal content for harvest of said metabolite of interest in the harvestable parts of the engineered plant is reached, and (iii) identifying a corresponding plant property (like plant growth stage) as an indicator of the optimal metabolite of interest content for harvest in the engineered plant.

However, the invention is not limited to methods for determining the optimal content of a metabolite of interest in view of harvesting the harvestable parts or the metabolite of interest in particular. The method can be applied in view of any treatment or processing of the engineered plants. Therefore, the invention also provides a method for determining a growth stage or other plant property at which the optimal content of a metabolite of interest is reached in a harvestable part of an engineered plant, wherein the synthesis of the metabolite of interest is modulated through a genetic modification, and which method comprises (i) cultivating the engineered plant and making a correlation between an accumulation pattern of the metabolite of interest and the plant growth stage or other plant property, (ii) determining the point in time at which the optimal content of said metabolite of interest in the harvestable parts of the engineered plant is reached, and (iii) identifying a corresponding plant growth stage or other plant property as an indicator of optimal metabolite of interest content in the engineered plant.

The term "engineered plant" refers to a plant of which the genome is modified through human intervention in such a way that a new trait which does not occur naturally in the plant species is introduced, for example altered or de novo production of a metabolite of interest. The genetic modification can be introduced by genetic engineering, genome editing or mutagenesis of the plant. In a preferred embodiment, the engineered plant is a transgenic plant, more preferably a transgenic plant capable of producing non-endogenous VLCPUFAs, most preferably capable of producing EPA and/or DHA.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the metabolite of interest. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. In a preferred embodiment, the plant is an oil crop, such as *Brassica napus, Helianthus annuus, Glycine soja, Zea mays, Carthamus tinctorius, Arachis hypogaea, Ricinus communis, Cocos nucifera, Elaeis guineensis, Olea europaea, Butyrospermum parkii, Aleurites cordata, Aleurites fordii, Simmondsia californica, Sesamum indicum, Sinapis alba, Brassica nigra*, amongst others. In a more preferred embodiment, the plant is *Brassica napus*, in particular canola.

Harvestable parts can be any plant part such as for example fruits, seeds, leaves, flowers, stems, above-ground biomass, roots, tubers, bulbs, rhizomes etc. Preferably the harvestable parts are seeds. In a preferred embodiment, the harvestable parts have the optimal content of the metabolite of interest at the time of harvest.

The term "metabolite of interest" as used herein refers to one or more particular metabolites whose production is to be modulated, be it increased or decreased. Preferably, the metabolite of interest has economic value, either as such or in a modified form. It should be clear that the metabolite of interest can be a single metabolite, multiple metabolites or a class of metabolites. The "metabolite of interest" can be a metabolite previously not synthesized by the plant, or it can be an endogenous metabolite whose synthesis is modulated. The "metabolite of interest" is typically produced by enzymes and does not encompass transcripts, peptides or polypeptides encoded by transgenes in the engineered plant. Preferably the metabolite of interest is a VLCPUFA, more preferably EPA and/or DHA.

The term "optimal content" or "accumulation level" as used herein applies to the desired or economically relevant concentration of the metabolite of interest in the harvestable parts of the engineered plant. In many cases, a concentration range around the desired concentration will be defined, the range then represents a lower and upper limit of acceptable concentrations for the metabolite of interest. The concentration of the metabolite of interest can be increased or decreased in the engineered plants compared to the corresponding control plants, depending on the nature of the metabolite of interest. For example, decreased concentrations can be aimed for where the metabolite of interest has toxic or otherwise undesired properties. Thus the term "accumulation pattern" refers to the synthesis of the metabolite of interest over time. For example the synthesis can be constant over time (steady state) or it can increase in the beginning, peak at a certain point in time and decrease thereafter. The term "accumulation pattern" encompasses the pattern of an overall increase as well as the pattern of an overall decrease in content of the metabolite of interest. In a preferred embodiment, where the metabolite of interest is a VLCPUFA, in particular a VLCPUFA that does not naturally occur in the non-engineered plant, the optimal content is an increased content. The increased content is, in increasing order of preference at least 1%, 2%, 3%, 4%, 5%, 6%, 7%, 8%, 9%, 10%, 11%, 12%, 13%, 14%, 15% of the total fatty acid content.

In a particular embodiment, the non-naturally occurring VLCPUFA is EPA and DHA that are synthesised de novo to a combined accumulation level of at least 5%, at least 6%, at least 7%, preferably at least 8%, further preferably at least 9%, further preferably at least 10%, more preferably at least 11%, most preferably at least 12% or higher of total fatty acid content. Where multiple metabolites of interest are involved, the term "optimal content" also comprises a desired composition or desired ratio in concentrations of the metabolites of interest. In another embodiment, the VLCPUFA is EPA and DHA that are synthesised de novo to a combined accumulation level of 7 to 15%, preferably 7 to 14%, more preferably 7 to 13%, most preferably 7 to 12% of total fatty acid content.

The choice of suitable control plants is a routine part of an experimental setup and may include corresponding wild-type plants or corresponding non-engineered plants. The control plant is typically of the same plant species or even of the same variety as the plant to be assessed. A "control plant" as used herein refers not only to whole plants, but also encompasses plant parts, including seeds and seed parts.

Plant properties can be any phenotypic trait of a plant that can be measured or observed, such as—but not limited to—a particular growth stage, plant height, number of leaves on the stem or rosette, transition from vegetative to reproductive stage, start of flowering, fruit or seed ripening, plant coloration like yellowing of leaves upon reaching maturity, seed pigment content, etc. Measurable plant properties can also include accumulation patterns of metabolites other than the metabolite of interest, as such metabolites may be easier to detect or quantified than the metabolite of interest and their accumulation patterns may be predictive for the accumulation level of the metabolite of interest, either in a direct way or in an inverse way. Agriculture nowadays makes use of modern techniques like hyperspectral imaging, which allows for the monitoring of various parameters like growth rates, leaf area index, leaf nitrogen content, pigment concentration, light use efficiency, canopy cover and some biochemical characteristics. All these parameters can be useful for assessing the growth stage of a plant. A preferred plant property is the transition from vegetative to reproductive stage, in particular the start of flowering, more particularly the opening of the first flower.

The engineered plants can be grown for example in the greenhouse or under field conditions. Under field conditions, determination of the optimal content of a metabolite of interest versus plant growth stage may require multiple cultivation rounds over different seasons, years and/or on different locations because environmental conditions (like weather conditions, soil conditions) may have an impact on plant growth and consequently on the accumulation pattern of the metabolite of interest. Also for plants grown in greenhouses, determination of the optimal content of a metabolite of interest versus plant growth stage must be carefully done, because, although the growing conditions are highly standardised, individual greenhouses may differ slightly from one another.

The invention can also take external factors into account. A typical example is the concept of Growing Degree Days (GDD) where the plant property (minimal temperature at which the plant grows) is combined with environmental parameters (day temperatures during the growing season). Taking canola as an example, North Dakota State University has provided a basic outline of *Brassica napus* growth and development with respect to growing degree days accumulated and uses 41° F. as the minimal threshold according to the formula below: The Daily Average Temp (° F.)=(Daily Max Temp ° F.+Daily Min Temp ° F.)/2, and Daily Canola GDD (° F.)=Daily Average Temperature ° F.−41° F.

Constraints on maximum and minimum temperatures are used to eliminate the effects of low or high temperatures that prevent or retard growth. For canola there is only a low-temperature constraint; if the daily Max and/or Min Temp<41° F., the daily Max and/or Min Temp is set equal to 41° F. The GDD can also be calculated using ° C. instead of ° F. Daily Canola GDD for each day can be summed to determine the accumulated GDD over a set time period.

Ideally the temperatures are measured at, or in close proximity to, the site where the engineered plants are cultivated. Alternatively, data from the nearest weather station can be used. Temperatures can be measured at different times during the day, but are preferably monitored in such a way that the maximal and minimal temperature during the day are known. Variants to the above method are possible, as long as the chosen method is consistently used. Alternatively, one could rely on historic data for a given crop and a given geographical location for calculating the GDD.

In an alternative embodiment, the invention provides a method for determining the optimal content of a metabolite of interest in harvestable parts of an engineered plant, which method makes use of the GDD concept. In this approach the engineered plants are grown until the life cycle is completed, or at least until a stage where the harvestable parts comprising the metabolite of interest have reached a suitable developmental stage or maturity; this may also imply choosing a suitable geographical location for growing the engineered plants. While monitoring plant growth and the daily temperatures, the accumulation of the metabolite of interest in the engineered plant or in its harvestable parts is recorded and the point in time of reaching the optimal content of the metabolite of interest is determined. Next, a specific and unambiguous developmental stage of the engineered plant is chosen as starting point for measuring the GDD, and the GDD are calculated from this starting point to the point in time where the optimal content of the metabolite of interest is reached. The accumulated GDD value is then an indicator for the developmental stage at which the optimal content of a metabolite of interest is reached in the engineered plant.

Therefore, the present invention provides a method for determining the growth stage at which the optimal content of a metabolite of interest is reached in harvestable parts of an engineered plant and expressing it as a GDD value, wherein the synthesis of said metabolite of interest is modulated through a genetic modification, and which method comprises
(i) choosing a suitable planting day;
(ii) recording the daily average temperature during growth of the engineered plant;
(iii) determining the point in time during plant growth at which the optimal content of the metabolite of interest in the harvestable parts of the engineered plant is reached;
(iv) determining a suitable starting point during plant growth for calculating the GDD to the point in time where the optimal content of the metabolite of interest in the harvestable parts of the engineered plant is reached; and
(v) determining the accumulated GDD from the starting point of (iii) to the point in time where the optimal content of the metabolite of interest in the harvestable parts is reached.

The planting day can be chosen such that the harvestable parts of the engineered plant can reach a suitable or desired developmental stage. Where the harvestable parts are seeds, a suitable developmental stage can be when all the seeds have matured, or when a certain percentage of the seeds have reached maturity.

Preferably the engineered plant is a transgenic plant, more preferably a transgenic oil crop, most preferably transgenic *Brassica napus*. Further preferably, the metabolite of interest is a non-endogenous VLCPUFA, more preferably the metabolite of interest is EPA and/or DHA. The starting point during plant growth for calculating the GDD to the point in time where the optimal content of the metabolite of interest in the harvestable parts of the engineered plant is reached can be various: the time of sowing, start of seed germination, the time point where plants have reached a particular height, the transition from vegetative to reproductive stage, the start of seed filling, etc. In a preferred embodiment, the starting point for calculating the GDD is the start of flowering.

The accumulated GDD value can then be used for making decisions with respect to harvesting or other treatments in preparation of harvesting the crop. For example, when growing engineered canola, the accumulated GGD value gives guidance for deciding when to start swathing, or when growing engineered potatoes, the accumulated GDD value may give guidance for spraying to desiccate the potato plants.

To date, no study has been published pertaining to EPA and DHA production in terrestrial transgenic plants. For example, it is not known if EPA and DHA concentration in seed oil is highest in young green seeds or in fully developed seeds, and therefore it is not possible to fully optimize field performance with respect to geographic locations, planting dates, harvest dates, and/or germplasm such that EPA and DHA content is maximized.

Multiple field trials were conducted using transgenic canola to explore how the activity of transgenes (T) is impacted by the environment where the plant is grown (E) (T×E interaction). Specifically, knowledge of the T×E interaction can be highly useful in the selection of geographic locations, planting dates, harvest dates, and/or germplasm such that the metabolite of interest content is optimally maximized. In a time course experiment it was observed that the concentration of EPA and DHA changes during seed development and that maximum EPA and DHA levels are observed at a specific seed maturity stage. Many aspects of plant development, including seed maturation, are regulated by temperature. Growing degree days (GDD) is a measure of heat experienced by a crop over a period of time. It was found that the maximum EPA and DHA concentration was obtained within a specific range of GDD values when measured from the time of flowering to the time of swathing or harvest. Monitoring GDD throughout the growing season and swathing or harvesting transgenic EPA and DHA producing canola within a predetermined GDD range is thus an easy and reliable way of obtaining maximal EPA and DHA levels in canola oil. This information could also be used to make informed decisions about planting geography, planting date, or germplasm selection in order to achieve a certain GDD. Physiological indicators can also be used to assess maturity of canola seeds and are frequently used to determine swathing time. According to the Canola Council of Canada, a canola crop is ready to be swathed when 60% of the seeds on the main stem have changed from green to brown in colour.

The invention thus also provides a method for determining the optimal time for swathing or harvesting of genetically engineered *Brassica* species that synthesize a VLCPUFA, and in particular EPA and/or DHA in the seeds. This method comprises
(i) choosing a suitable planting day for growing the plants and allow the seeds to reach the desired maturity;
(ii) recording the daily temperatures during growth of the transformed *Brassica* sp. for calculating the GDD;
(iii) sampling the transformed *Brassica* sp. plants, determining the accumulation of the VLCPUFA, and in particular EPA and/or DHA, in the developing and/or mature seeds, and defining the point in time at which the maximal level of the VLCPUFA, and in particular EPA and/or DHA in the seeds is reached;
(iv) monitoring the GDD from a desired growth stage, preferably from the start of flowering, to the point in time where the maximal content of the VLCPUFA, and in particular EPA and/or DHA in the seeds is reached, and
(v) calculating the accumulated GDD from the start of flowering to the point in time where the maximal content of the VLCPUFA, and in particular EPA and/or DHA in the seeds is reached.

The accumulated GDD value in this way obtained is a good predictor of the swathing or harvesting time for the transformed *Brassica* sp. plants.

For engineered plants grown in the field, it is useful to determine a range of GDD around the GDD value representing the time point where the optimal content of the metabolite of interest is reached, thereby creating an optimal window that gives a certain degree of flexibility in harvesting time or other treatment of the crop. This range may vary depending on the engineered plant species/variety and/or on the metabolite of interest and is ideally calculated on a case by case basis.

The present invention also provides a method for the commercial production of oil enriched with VLCPUFAs in a transgenic *Brassica napus* variety capable of producing VLCPUFAs, more particular EPA and/or DHA, which method comprises calculating the Growing Degree Days (GDD) in ° F., starting from the appearance of the first open flower, swathing the plants when the GDD reaches a value of at least 1600, harvesting the seeds at a suitable maturation stage and processing the seeds to produce oil enriched in VLCPUFAs.

In relation to the present invention, the timing of accumulation of naturally occurring PUFAs, namely linoleic (18:2n-6) and linolenic (18:3n-3) acids, in canola has been studied and reported. A detailed discussion of this matter is provided in the examples below. In general, the amount of 18:2n-6 and 18:3n-3 decreases as canola seeds age and reaches a minimum in fully mature seeds (Baux et al. 2008 Europ. J. Agronomy 29:102-107, Deng and Scarth 1998 JAOCS 75:759-766, and Fowler and Downey, 1970 Can. J. Plant. Sci. 50:233-247). In particular, Baux et al (supra) report that alpha-linolenic acid synthesis occurred mainly between 550 and 850 GDD after the onset of flowering, although during this time the concentration of alpha-linolenic acid decreased. Baux et al calculated GDD using ° C., which can be converted to GDD ° F. as described in Example 1. Additionally, Baux et al used a base temperature (Tbase) of 0° C., while the present invention specifies a Tbase of 41° F., or 5° C. Taking these differences into account, the GDD range reported by Baux converts to approximately 620-1160 GDD, calculated in ° F. with a Tbase of 41° F.

As outlined further below in the accompanying examples, the inventors calculated the GDD for VLCPUFA accumulation in a transgenic *Brassica napus* variety capable of producing the VLCPUFAs EPA and DHA. Examples 1 and 2 demonstrate that EPA and DHA content tends to reach a higher concentration in seeds that have accumulated the most GDD from flowering to swathing. The optimal GDD for VLCPUFA accumulation in such a transgenic *Brassica napus* variety is in excess of 1600, with the GDD calculated in ° F. and with a Tbase of 41° F. Example 3 demonstrates that this GDD value for EPA and DHA production is stable over at least three generations of the transgenic *Brassica napus* variety.

Therefore, the timing of EPA and DHA as expressed in GDD in the transgenic *Brassica napus* variety capable of producing the VLCPUFA is not consistent with the accumulation of naturally occurring PUFA in this species, and certainly could not have been predicted from the publications discussed herein.

Accordingly, in one embodiment, the plants are swathed with increasing preference, in a GDD range between 1600 and 2200, between 1600 and 2100 GDD, between 1600 and 2000 GDD, between 1600 and 1900 GDD, between 1600 and 1800 GDD, with the GDD calculated in ° F.

A further embodiment of this aspect of the invention is wherein seed from said plant has an oil content of at least 20%, preferable about 25%, about 30%, about 35%, about 40% or about 50%, for example between 20% and 55%, e.g. 30% and 50%, or 35 to 45% based on the total seed weight. A further embodiment of this aspect of the invention is wherein the oil contains EPA and DHA. Preferably the oil has a EPA and DHA content of about 3%, about 4%, about 5%, about 6%, about 8%, about 10%, about 12%, about 15%, about 17%, about 20% or about 25%, for example between 4% and 25%, 5% and 20%, 10% and 20% or 6% to 15% based on the total fatty acid content. A further embodiment of this aspect of the invention is wherein the oil is extracted from the plant, preferably from the seeds.

In the accompanying examples, the inventors calculated the GDD value for optimising VLCPUFA yield for a transgenic *Brassica napus* variety capable of producing EPA and DHA. The inventors calculated the GDD value using the time of flowering as a starting point and the time of swathing as the end point. Using this approach the inventors calculated a GDD value, and as shown in Example 3 this GDD value is stable over plant generations and is independent of production environment. It therefore can be appreciated that this method of calculating GDD can have broader utility than the specific transgenic *Brassica napus* variety used herein and also can be used for a range of different methods.

Accordingly, a further aspect of the invention provides a method for identifying the GDD time of harvest of a transgenic plant capable of producing VLCPUFA wherein GDD is calculated from flowering to swathing. As can be appreciated by the skilled person, the timing of harvest will be the GDD value which provides the optimal yield of VLCPUFA. Methods of calculating GDD are provided above in relation to other aspects of the invention, and also apply to this method of the invention.

Preferably the VLCPUFA comprise EPA and DHA. Preferably the transgenic plant is a transgenic *Brassica napus* variety capable of producing EPA and DHA.

Biosynthesis of LC-PUFA in organisms such as microalgae, mosses and fungi may occur by a series of alternating oxygendependent desaturations and elongation reactions. In one pathway, the desaturation reactions are catalysed by desaturases, while each of a elongase reaction adds a two-carbon unit to lengthen the chain. The conversion of ALA to DHA in these organisms therefore requires three desaturations and two elongations. Genes encoding the enzymes required for the production of DHA in this aerobic pathway have been cloned.

The conversion of ALA to ETA may be carried out by a combination of a d9 elongase and a d8 desaturase (the so-called d8 desaturation), the so-called "Sprecher" pathway, independent of a d4 desaturase (Sprecher et al. (1995) J. Lipid Res. 36:2471-2477.) or, through an anaerobic pathway (Abbadi et al. (2001) Eur. J. Lipid. Sci. Technol. 103:106-113.). The operons encoding these polyketide synthase (PKS) enzyme complexes have been cloned from some bacteria (Morita et al. (2000) Biochem. Soc. Trans. 28.:872-879.; Yu et al. (2000) Lipids 35: 1061-1064.; WO 00/42195).

The genes of each of these pathways can be introduced into the plants, resulting in the production of PUFAs.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term relates to long chain PUFA (VLC-PUFA) having from 20 to 24 carbon atoms in the fatty acid chain. Particularly, polyunsaturated fatty acids in the sense of the present invention are DHGLA 20:3 (8,11,14), ARA 20:4 (5,8,11,14), iARA 20:4(8,11,14,17), EPA 20:5 (5,8,11,14,17), DPA 22:5 (4,7,10,13,16), DHA 22:6 (4,7,10,13,16,19), 20:4 (8,11,14,17), more preferably, arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19).

The fatty acid esters with polyunsaturated C20- and/or C22-fatty acid molecules can be isolated in the form of an oil or lipid, for example, in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetylcoenzyme A esters which comprise the polyunsaturated fatty acids with at least two, three, four, five or six, preferably five or six, double bonds, from the organisms which were used for the preparation of the fatty acid esters. Preferably, they are isolated in the form of their diacylglycerides, triacylglycerides and/or in the form of phosphatidylcholine, especially preferably in the form of the triacylglycerides. In addition to these esters, the polyunsaturated fatty acids are also present in the non-human transgenic organisms or host cells, preferably in the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight. In the methods of the invention, the VLC-PUFAs produced are produced in a content as for DHA of at least 5,5% by weight, at least 6% by weight, at least 7% by weight, advantageously at least 8% by weight, preferably at least 9% by weight, especially preferably at least 10,5% by weight, very especially preferably at least 20% by weight, as for EPA of at least 9,5% by weight, at least 10% by weight, at least 11% by weight, advantageously at least 12% by weight, preferably at least 13% by weight, especially preferably at least 14,5% by weight, very especially preferably at least 30% by weight based on the total fatty acids in the non-human transgenic organisms or the host cell referred to above. The fatty acids are, preferably, produced in bound form. It is possible, with the aid of the polynucleotides and polypeptides of the present invention, for these unsaturated fatty acids to be positioned at the sn1, sn2 and/or sn3 position of the triglycerides which are, preferably, to be produced.

Preferred enzymes are in this context the desaturases and elongases as mentioned below, but also polynucleotide encoding an enzyme having delta-8-desaturase and/or ddelta-9-elongase activity. All these enzymes reflect the individual steps according to which the end products of the method of the present invention, for example EPA or DHA are produced from the starting compounds linoleic acid (C18:2) or linolenic acid (C18:3). As a rule, these compounds are not generated as essentially pure products. Rather, small traces of the precursors may be also present in the end product. If, for example, both linoleic acid and linolenic acid are present in the starting host cell, organism, or the starting plant, the end products, such as EPA or DHA, are present as mixtures. The precursors should advantageously not amount to more than 20% by weight, preferably not to more than 15% by weight, more preferably, not to more than 10% by weight, most preferably not to more than 5% by weight, based on the amount of the end product in question. Advantageously, only EPA or more preferably only DHA, bound or as free acids, is/are produced as end product(s) in the process of the invention in a host cell. If the compounds EPA and DHA are produced simultaneously, they are, preferably, produced in a ratio of at least 1:2 (DHA:EPA), more preferably, the ratios are at least 1:5 and, most preferably, 1:8. Fatty acid esters or fatty acid mixtures produced by the invention, preferably, comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms.

The term "desaturase" encompasses all enzymatic activities and enzymes catalyzing the desaturation of fatty acids with different lengths and numbers of unsaturated carbon atom double bonds. Specifically this includes delta 4 (d4)-desaturase, catalyzing the dehydrogenation of the 4th and 5th carbon atom; Delta 5 (d5)-desaturase catalyzing the dehydrogenation of the 5th and 6th carbon atom; Delta 6 (d6)-desaturase catalyzing the dehydrogenation of the 6th and 7th carbon atom; Delta 8 (d8)-desaturase catalyzing the dehydrogenation of the 8th and 9th carbon atom; Delta 9 (d9)-desaturase catalyzing the dehydrogenation of the 9th and 10th carbon atom; Delta 12 (d12)-desaturase catalyzing the dehydrogenation of the 12th and 13th carbon atom; Delta 15 (d15)-desaturase catalyzing the dehydrogenation of the 15th and 16th carbon atom.

The terms "elongase" encompasses all enzymatic activities and enzymes catalyzing the elongation of fatty acids with different lengths and numbers of unsaturated carbon atom double bonds. Especially the term "elongase" as used herein refers to the activity of an elongase, introducing two carbon molecules into the carbon chain of a fatty acid, preferably in the positions 5, 6, 9, 12 and/or 15 of fatty acids.

The production of LC-PUFA such as EPA and DHA involves more complicated engineering due to the increased number of desaturation and elongation steps involved. EPA production in a land plant was first reported by Qi et al. (2004) (Qi et al. (2004) Nat. Biotech. 22: 739-745) who introduced genes encoding a d9-elongase from *Isochtysis galbana*, a d8-desaturase from *Euglena gracilis* and a desaturase from *Mortierella alpina* into *Arabidopsis* yielding up to 3% EPA.

This work was followed by Abbadi et al. (2004) Plant Cell 16: 2734-2748. who reported the production of up to 0.8% EPA in flax seed using genes encoding a d6-desaturase and d6-elongase from *Physcomitrella patens* and a d5-desaturase from *Phaeodactylum tricornutum*.

A report of DHA production was in WO 04/017467 where the production of 3% DHA in soybean embryos is described, but not seed, by introducing genes encoding the *Saprolegnia diclina* d6-desaturase, *Mortierella alpina* d6-desaturase, *Mortierella alpina* d5-desaturase, *Saprolegnia diclina* d4-desaturase, *Saprolegnia diclina* d17-desaturase, *Mortierella alpina* d6-elongase and *Pavlova lutheri* d5-elongase.

In 2005, Wu et al. published (Wu et al. (2005) Nat. Biotech. 23:1013-1017) the production of ARA, EPA, and DHA in *Brassica juncea* using the *Pythium irregulare*, d6-desaturase, a Thraustochytrid d5-desaturase, the *Physcomitrella patens* d6-elongase, the Calendula officialis d12-desaturase, a Thraustochytrid d5-elongase, the *Phytophthora infestans* d17-desaturase, the *Oncorhyncus mykiss* LC-PUFA elongase, a Thraustochytrid d4-desaturase and a Thraustochytrid LPCAT (Wu et al. (2005) Nat. Biotech. 23:1013-1017).

LC-PUFA metabolic engineering in plant has been performed using the aerobic d6-desaturation/elongation pathway.

Thus, in one aspect a d6-desaturase, d5-desaturase, d6-elongase, d12-desaturase, d5-elongase, e.g. in combination with a d17-desaturase, a d4-desaturase and a LPCAT (Wu et al. (2005) Nat. Biotech. 23:1013-1017) are introduced into the plant of the present method.

In a further aspect, the plant for the production of EPA and/or DHA as used in the methods of the invention comprises exogenous polynucleotides encoding one of the following sets of enzymes;
i) an omega3-desaturase, a d6-desaturase, a d5-desaturase, a d4-desaturase, a d6-elongase and a d5-elongase,
ii) a d15-desaturase, a d6-desaturase, a d5-desaturase, a d4-desaturase, a d6-elongase and a d5-elongase,
iii) a d12-desaturase, a d6-desaturase, a d5-desaturase, a d4-desaturase, a d6-elongase and an d5-elongase,
iv) a d12-desaturase, a omega3-desaturase or a d15-desaturase, a d6-desaturase, a d5-desaturase, a d4-desaturase, a d6-elongase and an d5-elongase,
v) an omega3-desaturase, a d8-desaturase, a d5-desaturase, a d4-desaturase, a d9-elongase and an d5-elongase,
vi) a d15-desaturase, a d8-desaturase, a d5-desaturase, a d4-desaturase, a d9-elongase and a d5-elongase,
vii) a d12-desaturase, a d8-desaturase, a d5-desaturase, a d4-desaturase, a d9-elongase and an d5-elongase, or
viii) a d12-desaturase, a omega3-desaturase or a d15-desaturase, a d8-desaturase, a d5-desaturase, a d4-desaturase, a d9-elongase and an d5-elongase, and wherein each polynucleotide is operably linked to one or more promoters that are capable of directing expression of said polynucleotides in the cell.

In one aspect of the invention the plant for producing EPA and/or DHA expresses exogenous polynucleotides encoding one or more of the following enzymes of the VLC-PUFA biosynthetic pathway: Delta-6 ELONGASE; Delta-5 DESATURASE; Delta-6 DESATURASE, eg in combination with one or more of the following activities. Delta-6 ELONGASE; Delta-12 DESATURASE; Omega-3 DESATURASE; Omega-3-DESATURASE.

For example the plant used in the methods of the invention expresses polynucleotides encoding the following enzymes of the VLC-PUFA biosynthetic pathway: Delta-6 ELONGASE from *Physcomitrella patens*; Delta-5 DESATURASE from *Thraustochytrium* sp. ATCC21685; Delta-6 DESATURASE from *Ostreococcus tauri*; Delta-6 ELONGASE from *Thalassiosira pseudonana*; Delta-12 DESATURASE from *Phythophthora sojae*; Omega-3 DESATURASE from *Pythium irregulare*; Omega-3-DESATURASE from *Phythophthora infestans*; Delta-5 DESATURASE from *Thraustochytrium* sp. ATCC21685; Delta-4 DESATURASE from *Thraustochytrium* sp.; Omega-3 DESATURASE from *Pythium* irregular; Delta-4 DESATURASE from *Pavlova lutheri*; Delta-5 ELONGASE from *Ostreococcus tauri*.

Furthermore, the method used herein to calculate GDD values provides as an additional aspect of the invention a method for predicting the VLCPUFA content in seeds of a transgenic plant capable of producing VLCPUFA during the growth of said plant, wherein the quantity of VLCPUFA is measured and plotted against accumulated GDD. This aspect of the invention provides a means for determining the GDD value which predicts the optimal yield of VLCPUFA content of a plant. Preferably the VLCPUFA comprise EPA and DHA. Preferably the GDD is GDD41 from flowering to swathing. Preferably the transgenic plant is a transgenic *Brassica napus* variety capable of producing the EPA and DHA.

Still further, an additional aspect of the invention is a method for increasing the yield of oil comprising EPA and DHA, e.g. increasing the yield of EPA and DHA, produced by transgenic *B. napus* plants capable of producing VLCPUFA, e.g. EPA and DHA, at a location, e.g. in a region or field, or at particular environmental conditions, comprising breeding a transgenic plant capable of producing VLCPUFA into germplasm with flowering dates (or maturity times) such that an accumulated GDD41 of 1600 or more and 2200 or less, eg 1600 to 2000, or 1600 to 1800 from flowering to swathing at that location or that environmental conditions can be achieved for this germplasm, and selecting those progenies that have an accumulated GDD41 of at least 1600 and less than 2200, eg 1600 to 2000, or 1600 to 1800 from flowering to swathing at that location.

In one aspect, the germplasm selected for breeding shows flowering dates or maturity times such that at least 1600 and less than 2200 accumulated GDD41 from flowering to swathing can be achieved in any given location, e.g. in North Eastern United States (USA), e.g. Washington State, or Oregon. Thus, the present invention also relates to a corresponding *B. napus* plant that shows flowering dates or maturity times such that 1600 or more and 2200 or more accumulated GDD41 from flowering to swathing can be achieved in any given location, e.g. in North Eastern United States (USA), e.g. Washington State, or Oregon.

As outlined further below herein, the inventors calculated that the GDD for VLCPUFA accumulation in a transgenic *Brassica napus* variety capable of producing VLCPUFA DHA to generate the optimal yield of EPA and DHA is at least 1600. Accordingly, the invention also provides a method for the optimal yield of VLCPUFA from a transgenic plant comprising planting a transgenic plant able to produce VLCPUFA, wherein the planting date is chosen to provide the likelihood of achieving a desired GDD from flowering to swathing between 1600 and 2200. Preferably the VLCPUFA comprise EPA and DHA. Preferably the transgenic plant is a transgenic *Brassica napus* variety capable of producing the EPA and DHA. Preferably the transgenic *Brassica napus* variety is event LBFLFK, LBFGKN, LANPMZ or LAODDN as described in PCT/EP2015/076631 and all progeny or derivatives from said event. Preferably the transgenic *Brassica napus* variety is event LBFLFK. A preferred embodiment of this aspect of the invention is wherein the likelihood is determined by determining the average GDD in the planting location of at least the last 3, 4, 5 or more years, identifying the planting dates that allow to achieve 1600 and 2200 GDD, between 1600 and 2100 GDD, between 1600 and 2000 GDD, between 1600 and 1900 GDD, between 1600 and 1800 GDD, preferably GDD is GDD41.

Also provided herein is a further aspect of the invention which provides a method for generating seed comprising an VLCPUFA content of 4% and 25%, wherein a transgenic plant is grown from seeds of a transgenic plant capable of producing VLCPUFA, said method further comprising the step of swathing the transgenic plants when the GDD reaches a value of at least 1600. Preferably the VLCPUFA comprise EPA and DHA. Preferably the transgenic plant is a transgenic *Brassica napus* variety capable of producing the EPA and DHA. Preferably the EPA and DHA content is about 3%, about 4%, about 5%, about 6%, about 8%, about 10%, about 12%, about 15%, about 17%, about 20% or about 25%, for example between 4% and 25%, 5% and 20%, 10% and 20% or 6 to 15% based on the total fatty acid content.

In one embodiment, the transgenic *Brassica napus* variety used according the method of the invention is event LBFLFK, LBFGKN, LANPMZ or LAODDN as described in PCT/EP2015/076631 and all progeny or derivatives from said event, e.g. LBFLFK.

Still further aspects of the invention are provided below, which also relate to the inventors calculation that the GDD for VLCPUFA accumulation in a transgenic *Brassica napus* variety capable of producing VLCPUFA DHA to generate the optimal yield of EPA and DHA is 1600 or more and preferably 2200 or less, e.g. 2000, 1900 or 1800.

Hence, a further aspect of the invention provides a method to maximize the EPA and DHA yield per acre, comprising: (i) determining a location that allows 1600 to 2200, or 1600 to 2000, or 1600 to 1800 GDD41, (ii) selecting an appropriate germplasm/variety with flowering dates or maturity times such that 1600 or more and 2200 or less, e.g. 1600 to 2000 or 1600 to 2000, accumulated GDD41 from flowering to swathing can be achieved at said given location, (iii) choosing a flowering date that the desired GDD from flowering to swathing of 1600 to 2200, e.g. 1600 to 2000 or 1600 to 1800 can be achieved, growing the plants till maturity, and harvesting the seeds before late maturity.

A preferred embodiment of the aspects of the invention provided herein is wherein the GDD is calculated without a $T_{max}$ constraint.

A preferred embodiment of the aspects of the invention provided herein is wherein the GDD is GDD41.

A preferred embodiment of the aspects of the invention provided herein is wherein the harvest is before late maturity of the seed.

In a further aspect of the invention, the oil isolated according to the method of the invention is formulated to feed or food stuff, e.g. feed for aqua culture.

Items

1. A method for determining a growth stage or other plant property at which an optimal content of a metabolite of interest is reached in a harvestable part of an engineered plant, wherein the synthesis of said metabolite of interest is modulated through a genetic modification, and which method comprises:
    (i) cultivating the engineered plants and making a correlation between an accumulation pattern of the metabolite of interest and the plant growth stage or other plant property,
    (ii) determining a time at which the optimal content of said metabolite of interest in the harvestable parts of the engineered plant is reached, and
    (iii) identifying a corresponding plant growth stage or plant property as an indicator of the optimal content of the metabolite of interest in the engineered plant.
2. Method of item 1, wherein the genetic modification is introduced by genetic engineering, genome editing or mutagenesis of said engineered plant.
3. Method of item 1 or 2, wherein the engineered plant is a transgenic plant.
4. Method of item 3, wherein the transgenic plant is a transgenic oil crop, preferably a transgenic *Brassica* sp.
5. Method according to any of items 1 to 4, wherein the optimal content of a metabolite of interest is increased content compared to control plants.
6. Method according to any of items 1 to 5, wherein the metabolite of interest is not endogenous to the non-engineered plant.
7. Method according to any of items 1 to 4, wherein the optimal content of a metabolite of interest is decreased content compared to control plants.
8. Method according to any of items 1 to 7, wherein said optimal content of a metabolite of interest is the optimal content for harvesting said engineered plant.
9. Method according to any of items 1 to 6 and 8, wherein the metabolite of interest comprises a Very Long Chain Polyunsaturated Fatty Acid (VLCPUFA).
10. Method according to any of items 1 to 6 and 8, wherein the metabolite of interest is a non-endogenous VLCPUFA.
11. Method of item 9 or 10, wherein the VLCPUFA comprises eicosapentaenoic acid (EPA) and/or docosahexaenoic acid (DHA).
12. Method of item 10 or 11, wherein the non-endogenous VLCPUFA is eicosapentaenoic acid (EPA) and/or docosahexaenoic acid (DHA).
13. Method according to any of items 4 to 6 and 8 to 12, wherein the harvestable parts are fruits or seeds.
14. A method for determining the growth stage at which the optimal content of a metabolite of interest is reached in a harvestable part of an engineered plant and expressing it as a GDD value, wherein the synthesis of said metabolite of interest is modulated through a genetic modification, and which method comprises
    (i) choosing a suitable planting day;
    (ii) recording the daily average temperature during growth of the engineered plant;
    (iii) determining the point in time during plant growth at which the optimal content of the metabolite of interest in the harvestable parts of the engineered plant is reached;
    (iv) determining a suitable starting point during plant growth for calculating the GDD to the point in time where the optimal content of the metabolite of interest in the harvestable parts of the engineered plant is reached; and
    (v) determining the accumulated GDD from the starting point of (iii) to the point in time where the optimal content of the metabolite of interest in the harvestable parts is reached.
15. Method of item 14, wherein said planting day is chosen so as to allow the harvestable parts of said engineered plant reaching a desired developmental stage.
16. Method of item 14, wherein said daily average temperatures are recorded for calculating the GDD.
17. Method of item 14, wherein the metabolite of interest is not endogenous to the non-engineered plant.
18. Method of item 14, wherein the genetic modification is introduced by genetic engineering, genome editing or mutagenesis of said engineered plant.
19. Method of item 14, wherein the engineered plant is an oil crop, preferably a *Brassica* sp.
20. Method according to any of items 14 to 19, wherein the harvestable parts are fruits or seeds.
21. Method according to any of items 14 to 20, wherein the metabolite of interest comprises a VLCPUFA, preferably EPA and/or DHA.
22. Method according to any of items 14 to 20, wherein the metabolite of interest is a VLCPUFA, preferably EPA and/or DHA.
23. Method of item 14, wherein the GDD is used as a predictor for a suitable swathing or harvesting date.
24. Use of the method of item 1 or 14 for determining planting geography, planting date, or for germplasm selection of the engineered plant.
25. A method for determining the optimal time for swathing or harvesting of genetically engineered *Brassica* species that synthesize VLCPUFAs, preferably non-endogenous VLCPUFAs, and in particular EPA and/or DHA in seeds, which method comprises
(i) choosing a suitable planting day to allow the seeds to reach maturity;
(ii) recording the daily temperatures during growth of the transformed *Brassica* sp. for calculating the GDD;
(iii) sampling the transformed *Brassica* sp. plants, determining the accumulation of EPA and/or DHA in the developing and/or mature seeds, and defining the point in time at which the maximal level of EPA and/or DHA in the seeds is reached;
(iv) monitoring the GDD from the start of flowering to the point in time where the maximal content of EPA and/or DHA in the seeds is reached, and
(v) calculating the accumulated GDD from the start of flowering to the point in time where the maximal content of EPA and/or DHA in the seeds is reached.

26. Method of item 25, wherein a range of GDD is defined around the GDD value corresponding to the point in time where the maximal content of EPA and/or DHA in the seeds is reached.

27. Method of item 26 wherein the GDD value corresponding to the point in time where the maximal content of EPA and/or DHA in the seeds is reached is the bottom limit of the range.

28. A method for the commercial production of oil enriched with a VLCPUFA from seeds of a transgenic *Brassica napus* variety capable of producing said VLCPUFA, which method comprises:
(i) calculating the Growing Degree Days (GDD) in ° F., starting from the appearance of the first open flower,
(ii) swathing the plants when the GDD reaches a value of at least 1600,
(iii) harvesting the seeds at a suitable maturation stage and processing the seeds to produce oil enriched in said VLCPUFA.

29. Method of item 28, wherein the VLCPUFA is EPA and/or DHA.

30. Method of item 28 or 29, wherein the plants are swathed in a range of growing GDD between, with increasing order of preference, 1600 and 2200 GDD, between 1600 and 2100 GDD, between 1600 and 2000 GDD, between 1600 and 1900 GDD, between 1600 and 1800 GDD.

31. Method according to any of items 28 to 30 wherein seed from said plant has an oil content of 20% and 55%.

32. Method according to any of items 28 to 31 wherein the oil comprises EPA and/or DHA.

33. Method of item 32, wherein the oil has a EPA and DHA content of 4% and 25%.

34. Method according to any of items 28 to 33 wherein the oil is extracted from the plant.

35. A method for identifying the GDD time of harvest of a transgenic plant capable of producing VLCPUFA wherein GDD is calculated from flowering to swathing.

36. A method for predicting the VLCPUFA content in seeds of a transgenic plant capable of producing VLCPUFA during the growth of said plant, wherein the quantity of VLCPUFA is measured and plotted against accumulated GDD.

37. A method for the optimal yield of VLCPUFA from a transgenic plant in a location, wherein a transgenic plant capable of producing VLCPUFA is bred into germplasm with flowering dates (or maturity times) such that 1600 to 2000 accumulated GDD 41 from flowering to swathing at that location can be achieved.

38. A method for the optimal yield of VLCPUFA from a transgenic plant comprising planting a transgenic plant able to produce VLCPUFA, wherein the planting date is chosen to provide the likelihood of achieving a desired GDD from flowering to swathing between 1600 and 2200.

39. Method of item 38 wherein the likelihood is determined by determining the average GDD in the planting location of at least the last 3 years, identifying the planting dates that allow to achieve 1600 and 2200 GDD, between 1600 and 2100 GDD, between 1600 and 2000 GDD, between 1600 and 1900 GDD, between 1600 and 1800 GDD.

40. A method for generating seed comprising an VLCPUFA content of 4% and 25%, wherein a transgenic plant is grown from seeds of a transgenic plant capable of producing VLCPUFA, said method further comprising the step of swathing the transgenic plants when the GDD reaches a value of at least 1600.

41. A method to maximize the EPA and DHA yield per acre, comprising: (i) determining a location that allows 1600 to 2200 GDD41, (ii) selecting an appropriate germplasm/variety with flowering dates or maturity times such that at least 1600 accumulated GDD41 from flowering to swathing can be achieved at said given location, (iii) choosing a flowering date that the desired GDD from flowering to swathing of 1600 to 2200 can be achieved, growing the plants till maturity, and harvesting the seeds before late maturity.

42. Method according to any of items 35 to 41 wherein VLCPUFA comprise EPA and DHA.

43. Method according to any of items 35 to 41 wherein the transgenic plant is a transgenic
*Brassica napus* variety capable of producing EPA and DHA.

44. Method according to any of the previous items wherein the GDD is calculated without a $T_{max}$ constraint.

45. Method according to any of the previous items wherein the GDD is GDD41.

46. Method according to any of the previous items wherein the harvest is before late maturity of the seed.

DESCRIPTION OF FIGURES

The present invention is described with reference to the following figures in which.

EXAMPLES

Figure 1:
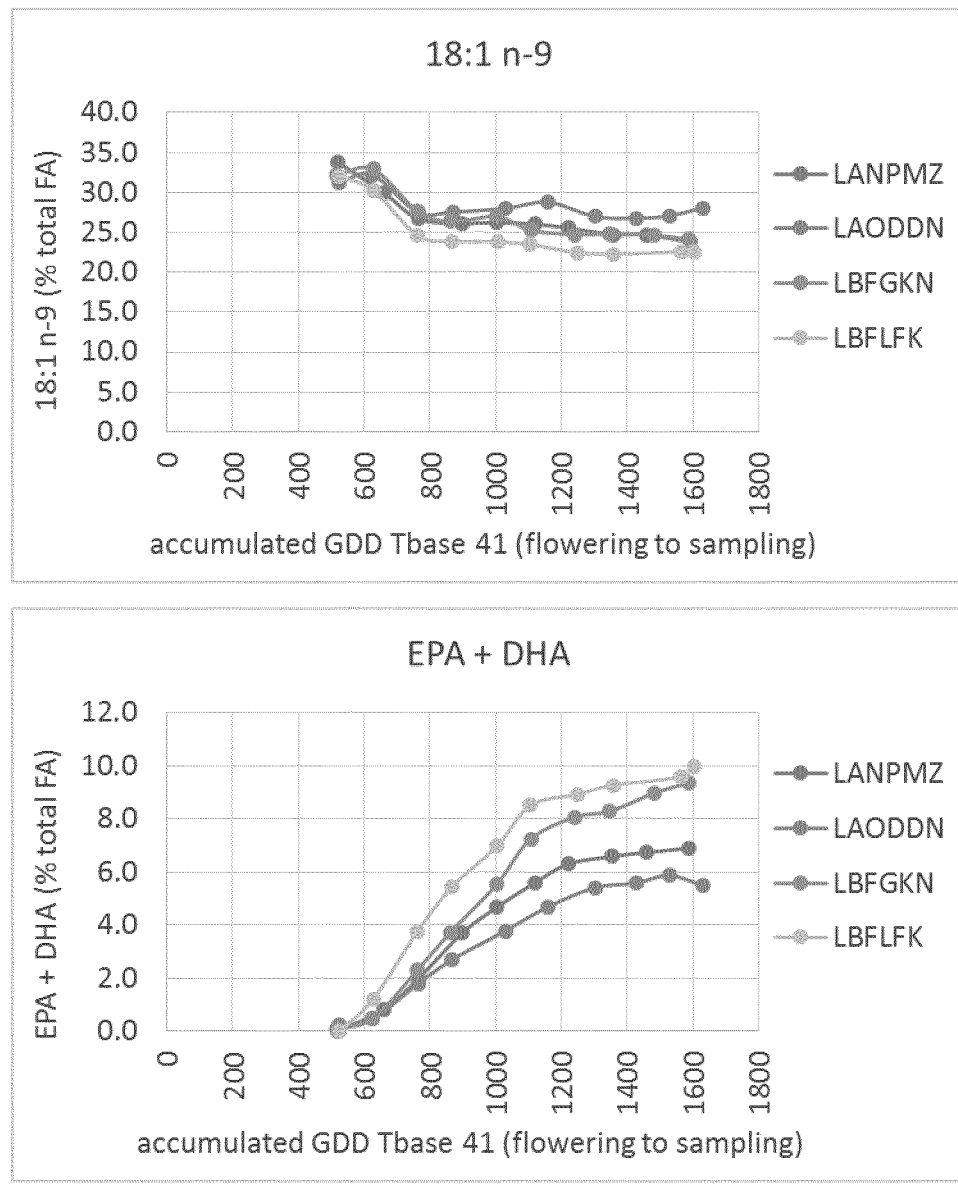
FIG. 1: Change in the concentration of 18:1 n-9 and EPA+DHA over GDD accumulation.

Example 1. PUFA Accumulation During Canola Seed Development

Plant Growth and Sampling

All plant vectors and events are described in PCT/EP2015/076631. Homozygous T3 or T4 plants of event LBFLFK, LBFGKN, LANPMZ and LAODDN were sown in the field in Hawaii in January. In the week following the date of first flower, individual racemes were visibly marked on the stem just above the most recently opened flower. For every raceme, the three pods immediately below the mark were considered to be the same age (i.e. flowered or were pollinated on the same day). Starting at 14 days after marking and until 46 days after marking, the three pods below the mark on each raceme were collected at various time points. At each time point, approximately 150 pods from 50 individual plants were sampled. Each individual plant was sampled only once in its lifespan. Immature seeds were dissected from the pods immediately after removal from the raceme and were promptly frozen on dry ice. The age of the seeds was determined by the age of the mark on the raceme, meaning that the three pods (and the seeds inside) taken from immediately below a 15 day-old mark were assumed to be 15 days after flowering. For each event, at each time point, seeds from about 150 pods were pooled into a single sample. For analysis, each seed sample was pulverized to powder while still frozen, and the powder was dispensed into aliquot amounts to be used as technical replicates for lipid analysis.

Lipid Extraction and Lipid Analysis of Plant Oils

Extraction of oil from canola seed samples was carried out by adding 800 µL of methyl tert-butyl ether (MTBE) to the samples followed by extraction in a swing mill for 2×30 sec at 30 Hz. After centrifugation at 4000 rpm for 10 min, 40 µL of the clear supernatant was transferred into a 96 well micro rack and diluted using 260 µL MTBE. Lipids were derivatized into fatty acid methyl esters (FAMEs) by adding 20 µL trimethylsulfonium hydroxide solution (TMSH, 0.2 M in methanol) into each sample. The rack was closed using silicone/PTFE cap mats and incubated for 20 min at room temperature.

An Agilent 7890A gas chromatograph coupled to Agilent flame ionization detector was used for FAME analysis. Separation of FAMEs was carried out on a DB-225 capillary column (20 m×180 µm×0.2 µm, Agilent) using H2 as carrier gas with a flow rate of 0.8 mL/min. The GC was operated in split mode using a split ratio of 1:50 at an injector temperature of 250° C., injection volume was 1 µL. Oven temperature was held at 190° C. for 3 min and increased to 220° C. with 15° C. min-1. Temperature was held at 220° C. for another 6 min. Peak detection and integration was carried out using Agilent GC ChemStation software (Rev. B.04.02 SP1). The content (levels) of fatty acids is expressed throughout the present invention as percentage (weight of a particular fatty acid) of the (total weight of all fatty acids).

Calculation of GDD

Growing degree day (GDD) accumulation was calculated using atmospheric data from the nearest weather station to each experimental plot. The GDD daily value=[($T_{max}$+Tmin)/2]−Tbase, where $T_{max}$ is the maximum daily temperature in degrees F. This value can be constrained to minimize the impact of high temperatures that can minimize growth. For calculating canola GDD, there is typically no constraint placed on $T_{max}$. Tmin is the minimum daily temperature in degrees F. Tbase is related to the minimum temperature at which a particular plant grows and is calculated by region. A typically accepted value of Tbase for canola is 41 degrees F. The accumulated GDD value is then the sum of all GDD daily values from a defined time to another defined time. GDD values may also be calculated using degrees C. A typical Tbase for canola is 5 degrees C. One can convert GDD from F to C by using the following conversion rate 9 GDD F=5 GDD C.

PUFA Production in Developing Canola Seeds

The fatty acid profiles of developing canola seeds is shown in Table 1. The age of each seed sample is indicated with days after flowering and with accumulated GDD from flowering to sampling calculated both with Tbase of 50 degrees (GDD50) F and with Tbase of 41 degrees F. (GDD41). Individual fatty acids have different accumulation patterns. For example, the precursor fatty acid for the transgenic biosynthetic pathway, 18:1n-9, declines rapidly and appears to reach a steady state at around 1000 GDD41 (FIG. 1). Between zero and 1005 GDD41 18:1 n-9 decreased from 32% to 23.8%, which is a relative decrease of 26%. From 1005 to 1604 GDD41 18:1n-9 decreased from 23.8% to 22.6%, which is a relative decrease of just 5%. However, EPA+DHA accumulates throughout developmental time, peaking at around 1600 GDD41 (FIG. 1). While 18:1n-9 changed by just 5% relative between 1005 and 1604 GDD41, EPA+DHA increased from 7 to 10%, which is a relative increase of 43%. This trend was observed for all four events examined, regardless of which construct(s) were used for transformation. The timing of EPA and DHA accumulation is not consistent with the accumulation of naturally occurring PUFAs in canola, namely linoleic (18:2n-6) and linolenic (18:3n-3) acids. In general, the amount of 18:2n-6 and 18:3n-3 decreases as canola seeds age and reaches a minimum in fully mature seeds (Baux et al. 2008 Europ. J. Agronomy 29:102-107, Deng and Scarth 1998 JAOCS 75:759-766, and Fowler and Downey, 1970 Can. J. Plant. Sci. 50:233-247).

TABLE 1a

Accumulated GDD from first flower to sampling and fatty acid profile from developing seeds of four canola events.
The content fatty acids is expressed as percentage (weight of a particular fatty acid) of the (total weight of all fatty acids).

| Event | Days After | Accumulated GDD first flower to sampling Tbase = 50 | Tbase = 41 | 16:0 | 16:1n-7 | 16:3n-3 | 18:0 | 18:1n-7 | 18:1n-9 | 18:2n-6 (LA) |
|---|---|---|---|---|---|---|---|---|---|---|
| LANPMZ | 14 | 394 | 520 | 7.4 | 1.2 | 0.3 | 4.3 | 13.1 | 33.7 | 29.6 |
| LANPMZ | 18 | 497 | 659 | 6.3 | 0.6 | 0.2 | 3.5 | 7.6 | 29.9 | 38.0 |
| LANPMZ | 21 | 575 | 764 | 5.7 | 0.5 | 0.1 | 3.2 | 6.0 | 26.7 | 40.6 |
| LANPMZ | 25 | 673 | 898 | 5.1 | 0.3 | 0.1 | 2.9 | 5.0 | 26.1 | 39.7 |
| LANPMZ | 28 | 751 | 1003 | 5.2 | 0.3 | 0.1 | 2.8 | 4.8 | 26.2 | 37.9 |
| LANPMZ | 32 | 832 | 1120 | 5.0 | 0.3 | 0.1 | 2.9 | 4.6 | 26.0 | 37.0 |
| LANPMZ | 35 | 907 | 1222 | 5.0 | 0.3 | 0.1 | 2.8 | 4.4 | 25.5 | 36.1 |
| LANPMZ | 39 | 1005 | 1356 | 5.0 | 0.3 | 0.1 | 2.7 | 4.4 | 24.7 | 36.2 |
| LANPMZ | 42 | 1080 | 1458 | 4.9 | 0.3 | 0.1 | 2.8 | 4.2 | 24.7 | 36.2 |
| LANPMZ | 46 | 1176 | 1590 | 5.1 | 0.4 | 0.1 | 2.8 | 4.3 | 23.8 | 36.4 |
| LAODDN | 14 | 399 | 525 | 7.5 | 1.5 | 0.3 | 4.4 | 15.3 | 31.2 | 29.7 |
| LAODDN | 17 | 472 | 625 | 7.2 | 0.8 | 0.2 | 4.1 | 9.2 | 32.2 | 34.8 |
| LAODDN | 21 | 575 | 764 | 5.8 | 0.5 | 0.1 | 3.1 | 5.9 | 27.4 | 42.0 |
| LAODDN | 24 | 653 | 869 | 5.1 | 0.4 | 0.1 | 2.8 | 4.8 | 27.5 | 42.1 |
| LAODDN | 28 | 777 | 1029 | 4.9 | 0.3 | 0.1 | 2.6 | 4.4 | 28.0 | 40.5 |
| LAODDN | 31 | 880 | 1159 | 4.8 | 0.3 | 0.1 | 2.6 | 4.2 | 28.7 | 38.1 |
| LAODDN | 35 | 988 | 1303 | 4.9 | 0.3 | 0.1 | 2.6 | 4.3 | 26.9 | 38.8 |
| LAODDN | 38 | 1085 | 1427 | 4.9 | 0.3 | 0.1 | 2.6 | 4.3 | 26.7 | 38.2 |
| LAODDN | 42 | 1150 | 1528 | 4.8 | 0.3 | 0.1 | 2.6 | 4.0 | 27.0 | 38.2 |
| LAODDN | 45 | 1225 | 1630 | 4.8 | 0.3 | 0.1 | 2.6 | 3.8 | 28.0 | 38.0 |
| LBFGKN | 14 | 391 | 517 | 7.5 | 1.5 | 0.4 | 3.9 | 16.3 | 32.1 | 27.7 |
| LBFGKN | 17 | 474 | 627 | 7.2 | 0.9 | 0.3 | 3.6 | 10.5 | 32.9 | 33.2 |
| LBFGKN | 21 | 574 | 763 | 6.1 | 0.6 | 0.2 | 3.1 | 7.1 | 27.6 | 39.7 |
| LBFGKN | 24 | 647 | 863 | 5.3 | 0.4 | 0.1 | 3.1 | 5.6 | 26.3 | 40.5 |
| LBFGKN | 28 | 752 | 1004 | 4.9 | 0.4 | 0.1 | 2.8 | 4.8 | 26.9 | 37.9 |
| LBFGKN | 31 | 828 | 1107 | 5.0 | 0.3 | 0.1 | 2.8 | 4.7 | 25.2 | 36.8 |
| LBFGKN | 35 | 927 | 1242 | 4.9 | 0.3 | 0.1 | 2.9 | 4.7 | 24.7 | 36.4 |
| LBFGKN | 38 | 1005 | 1347 | 4.9 | 0.3 | 0.1 | 2.9 | 4.5 | 24.8 | 36.4 |
| LBFGKN | 42 | 1105 | 1483 | 4.7 | 0.3 | 0.1 | 2.9 | 4.3 | 24.6 | 35.8 |
| LBFGKN | 45 | 1182 | 1587 | 4.8 | 0.3 | 0.1 | 2.8 | 4.3 | 24.1 | 35.6 |
| LBFLFK | 14 | 399 | 525 | 7.6 | 1.4 | 0.4 | 4.2 | 15.0 | 32.0 | 29.4 |
| LBFLFK | 17 | 475 | 628 | 7.1 | 0.8 | 0.2 | 3.7 | 8.9 | 30.2 | 36.2 |
| LBFLFK | 21 | 572 | 761 | 5.9 | 0.4 | 0.2 | 3.3 | 5.9 | 24.6 | 39.2 |
| LBFLFK | 24 | 651 | 867 | 5.5 | 0.3 | 0.1 | 2.9 | 4.9 | 23.9 | 38.1 |
| LBFLFK | 28 | 753 | 1005 | 5.1 | 0.3 | 0.1 | 2.9 | 4.5 | 23.8 | 34.4 |
| LBFLFK | 31 | 827 | 1106 | 5.1 | 0.3 | 0.1 | 2.8 | 4.5 | 23.4 | 33.3 |
| LBFLFK | 35 | 935 | 1250 | 5.1 | 0.3 | 0.1 | 2.9 | 4.4 | 22.4 | 33.1 |
| LBFLFK | 38 | 1015 | 1357 | 4.9 | 0.3 | 0.1 | 2.9 | 4.2 | 22.3 | 32.2 |
| LBFLFK | 45 | 1160 | 1565 | 5.0 | 0.3 | 0.1 | 2.9 | 4.2 | 22.5 | 32.1 |
| LBFLFK | 46 | 1190 | 1604 | 4.9 | 0.3 | 0.1 | 2.8 | 4.1 | 22.6 | 31.8 |

| Event | 18:2n-9 | 18:3n-3 (ALA) | 18:3n-6 (GLA) | 18:4n-3 (SDA) | 20:0 | 20:1n-9 | 20:2n-6 |
|---|---|---|---|---|---|---|---|
| LANPMZ | 0.0 | 7.6 | 0.0 | 0.0 | 1.0 | 0.5 | 0.1 |
| LANPMZ | 0.1 | 7.7 | 0.2 | 0.1 | 0.9 | 0.7 | 0.2 |
| LANPMZ | 0.2 | 6.8 | 0.5 | 0.1 | 0.8 | 0.7 | 0.3 |
| LANPMZ | 0.3 | 5.9 | 0.7 | 0.1 | 0.7 | 0.7 | 0.4 |
| LANPMZ | 0.3 | 5.6 | 0.8 | 0.1 | 0.7 | 0.7 | 0.4 |
| LANPMZ | 0.3 | 5.2 | 0.8 | 0.1 | 0.7 | 0.7 | 0.5 |
| LANPMZ | 0.3 | 5.1 | 0.8 | 0.1 | 0.7 | 0.7 | 0.5 |
| LANPMZ | 0.3 | 5.1 | 0.9 | 0.2 | 0.8 | 0.7 | 0.5 |
| LANPMZ | 0.3 | 5.2 | 0.9 | 0.2 | 0.7 | 0.7 | 0.5 |
| LANPMZ | 0.3 | 5.0 | 0.9 | 0.2 | 0.7 | 0.7 | 0.5 |
| LAODDN | 0.0 | 7.2 | 0.0 | 0.0 | 1.0 | 0.4 | 0.1 |
| LAODDN | 0.1 | 7.6 | 0.1 | 0.0 | 1.0 | 0.5 | 0.1 |
| LAODDN | 0.2 | 7.3 | 0.4 | 0.1 | 0.8 | 0.7 | 0.1 |
| LAODDN | 0.2 | 6.9 | 0.6 | 0.1 | 0.7 | 0.7 | 0.1 |
| LAODDN | 0.3 | 6.8 | 0.8 | 0.2 | 0.6 | 0.7 | 0.1 |
| LAODDN | 0.3 | 6.8 | 1.1 | 0.3 | 0.6 | 0.7 | 0.1 |
| LAODDN | 0.3 | 6.3 | 1.3 | 0.3 | 0.6 | 0.7 | 0.1 |
| LAODDN | 0.3 | 6.5 | 1.4 | 0.4 | 0.7 | 0.7 | 0.1 |
| LAODDN | 0.3 | 6.4 | 1.5 | 0.4 | 0.6 | 0.7 | 0.1 |
| LAODDN | 0.3 | 6.6 | 1.4 | 0.4 | 0.6 | 0.7 | 0.1 |
| LBFGKN | 0.0 | 7.8 | 0.0 | 0.0 | 0.9 | 0.4 | 0.1 |
| LBFGKN | 0.1 | 7.5 | 0.1 | 0.0 | 1.0 | 0.6 | 0.1 |
| LBFGKN | 0.2 | 6.7 | 0.6 | 0.1 | 0.8 | 0.6 | 0.1 |
| LBFGKN | 0.3 | 6.3 | 0.9 | 0.2 | 0.8 | 0.7 | 0.2 |
| LBFGKN | 0.4 | 5.7 | 1.1 | 0.2 | 0.7 | 0.7 | 0.2 |

TABLE 1a-continued

Accumulated GDD from first flower to sampling and fatty acid profile from developing seeds of four canola events. The content fatty acids is expressed as percentage (weight of a particular fatty acid) of the (total weight of all fatty acids).

| Event | | | | | | | |
|---|---|---|---|---|---|---|---|
| LBFGKN | 0.5 | 5.2 | 1.4 | 0.2 | 0.7 | 0.7 | 0.2 |
| LBFGKN | 0.5 | 5.1 | 1.4 | 0.2 | 0.7 | 0.7 | 0.2 |
| LBFGKN | 0.5 | 5.1 | 1.4 | 0.2 | 0.7 | 0.7 | 0.2 |
| LBFGKN | 0.5 | 5.1 | 1.4 | 0.2 | 0.8 | 0.7 | 0.2 |
| LBFGKN | 0.5 | 5.2 | 1.5 | 0.2 | 0.8 | 0.7 | 0.2 |
| LBFLFK | 0.0 | 7.4 | 0.0 | 0.0 | 1.0 | 0.4 | 0.1 |
| LBFLFK | 0.2 | 6.8 | 0.4 | 0.1 | 1.0 | 0.5 | 0.1 |
| LBFLFK | 0.5 | 6.0 | 1.2 | 0.2 | 0.8 | 0.6 | 0.1 |
| LBFLFK | 0.6 | 5.4 | 1.5 | 0.2 | 0.7 | 0.6 | 0.1 |
| LBFLFK | 0.8 | 4.6 | 2.0 | 0.2 | 0.7 | 0.6 | 0.1 |
| LBFLFK | 0.7 | 4.3 | 2.1 | 0.3 | 0.7 | 0.7 | 0.1 |
| LBFLFK | 0.8 | 4.0 | 2.2 | 0.3 | 0.7 | 0.6 | 0.1 |
| LBFLFK | 0.8 | 4.0 | 2.4 | 0.3 | 0.7 | 0.7 | 0.1 |
| LBFLFK | 0.8 | 4.1 | 2.2 | 0.3 | 0.8 | 0.6 | 0.1 |
| LBFLFK | 0.8 | 4.1 | 2.2 | 0.3 | 0.7 | 0.7 | 0.1 |

TABLE 1b

Accumulated GDD from first flower to sampling and fatty acid profile from developing seeds of four canola events. The content fatty acids is expressed as percentage (weight of a particular fatty acid) of the (total weight of all fatty acids).

| Event | Days After | Accumulated GDD first flower to sampling | | Fatty Acid Composition (% total FA) | | | | | |
|---|---|---|---|---|---|---|---|---|---|
| | | Tbase = 50 | Tbase = 41 | 20:2n-9 | 20:3n-3 | 20:3n-6 (DGLA) | 20:3n-9 | 20:4n-3 (ETA) | 20:4n-6 (ARA) |
| LANPMZ | 14 | 394 | 520 | 0.0 | 0.0 | 0.1 | 0.0 | 0.0 | 0.1 |
| LANPMZ | 18 | 497 | 659 | 0.0 | 0.1 | 0.3 | 0.0 | 0.1 | 0.9 |
| LANPMZ | 21 | 575 | 764 | 0.1 | 0.1 | 0.7 | 0.0 | 0.3 | 2.0 |
| LANPMZ | 25 | 673 | 898 | 0.2 | 0.1 | 1.0 | 0.1 | 0.5 | 2.8 |
| LANPMZ | 28 | 751 | 1003 | 0.2 | 0.1 | 1.2 | 0.1 | 0.6 | 3.1 |
| LANPMZ | 32 | 832 | 1120 | 0.2 | 0.1 | 1.4 | 0.1 | 0.7 | 3.3 |
| LANPMZ | 35 | 907 | 1222 | 0.2 | 0.2 | 1.6 | 0.1 | 0.8 | 3.6 |
| LANPMZ | 39 | 1005 | 1356 | 0.2 | 0.1 | 1.6 | 0.1 | 0.8 | 3.6 |
| LANPMZ | 42 | 1080 | 1458 | 0.2 | 0.2 | 1.7 | 0.1 | 0.9 | 3.6 |
| LANPMZ | 46 | 1176 | 1590 | 0.2 | 0.2 | 1.7 | 0.1 | 0.9 | 3.6 |
| LAODDN | 14 | 399 | 525 | 0.0 | 0.0 | 0.1 | 0.0 | 0.0 | 0.1 |
| LAODDN | 17 | 472 | 625 | 0.0 | 0.0 | 0.1 | 0.0 | 0.1 | 0.3 |
| LAODDN | 21 | 575 | 764 | 0.0 | 0.0 | 0.4 | 0.0 | 0.2 | 0.9 |
| LAODDN | 24 | 653 | 869 | 0.1 | 0.1 | 0.6 | 0.0 | 0.3 | 1.2 |
| LAODDN | 28 | 777 | 1029 | 0.1 | 0.1 | 0.6 | 0.0 | 0.4 | 1.5 |
| LAODDN | 31 | 880 | 1159 | 0.1 | 0.1 | 0.7 | 0.0 | 0.5 | 1.5 |
| LAODDN | 35 | 988 | 1303 | 0.1 | 0.1 | 0.8 | 0.0 | 0.5 | 1.5 |
| LAODDN | 38 | 1085 | 1427 | 0.1 | 0.1 | 0.8 | 0.0 | 0.6 | 1.4 |
| LAODDN | 42 | 1150 | 1528 | 0.1 | 0.1 | 0.8 | 0.0 | 0.6 | 1.4 |
| LAODDN | 45 | 1225 | 1630 | 0.1 | 0.1 | 0.7 | 0.0 | 0.6 | 1.3 |
| LBFGKN | 14 | 391 | 517 | 0.0 | 0.0 | 0.0 | 0.0 | 0.0 | 0.2 |
| LBFGKN | 17 | 474 | 627 | 0.0 | 0.0 | 0.1 | 0.0 | 0.1 | 0.3 |
| LBFGKN | 21 | 574 | 763 | 0.0 | 0.1 | 0.7 | 0.0 | 0.3 | 1.2 |
| LBFGKN | 24 | 647 | 863 | 0.1 | 0.1 | 1.0 | 0.0 | 0.4 | 1.8 |
| LBFGKN | 28 | 752 | 1004 | 0.1 | 0.1 | 1.4 | 0.0 | 0.6 | 2.6 |
| LBFGKN | 31 | 828 | 1107 | 0.1 | 0.1 | 1.7 | 0.1 | 0.7 | 3.0 |
| LBFGKN | 35 | 927 | 1242 | 0.1 | 0.1 | 1.8 | 0.1 | 0.9 | 2.8 |
| LBFGKN | 38 | 1005 | 1347 | 0.1 | 0.1 | 1.9 | 0.1 | 0.9 | 2.6 |
| LBFGKN | 42 | 1105 | 1483 | 0.1 | 0.1 | 1.9 | 0.1 | 1.0 | 2.6 |
| LBFGKN | 45 | 1182 | 1587 | 0.1 | 0.1 | 2.0 | 0.1 | 1.1 | 2.5 |
| LBFLFK | 14 | 399 | 525 | 0.0 | 0.0 | 0.1 | 0.0 | 0.0 | 0.2 |
| LBFLFK | 17 | 475 | 628 | 0.0 | 0.0 | 0.4 | 0.0 | 0.2 | 0.6 |
| LBFLFK | 21 | 572 | 761 | 0.1 | 0.1 | 1.9 | 0.0 | 0.7 | 1.9 |
| LBFLFK | 24 | 651 | 867 | 0.1 | 0.1 | 2.4 | 0.0 | 0.9 | 2.5 |
| LBFLFK | 28 | 753 | 1005 | 0.2 | 0.1 | 3.6 | 0.1 | 1.3 | 3.0 |
| LBFLFK | 31 | 827 | 1106 | 0.2 | 0.1 | 3.2 | 0.1 | 1.3 | 3.3 |
| LBFLFK | 35 | 935 | 1250 | 0.2 | 0.1 | 3.6 | 0.1 | 1.5 | 3.1 |
| LBFLFK | 38 | 1015 | 1357 | 0.2 | 0.1 | 4.2 | 0.1 | 1.8 | 2.8 |
| LBFLFK | 45 | 1160 | 1565 | 0.2 | 0.1 | 4.0 | 0.1 | 1.9 | 2.6 |
| LBFLFK | 46 | 1190 | 1604 | 0.2 | 0.1 | 3.9 | 0.1 | 1.9 | 2.5 |

TABLE 1b-continued

Accumulated GDD from first flower to sampling and fatty acid profile from developing seeds of four canola events. The content fatty acids is expressed as percentage (weight of a particular fatty acid) of the (total weight of all fatty acids).

| Event | Fatty Acid Composition (% total FA) | | | | | | |
|---|---|---|---|---|---|---|---|
| | 20:5n-3 (EPA) | 22:0 | 22:4n-3 | 224n-6 | 22:5n-3 (DPA) | 22:5n-6 | 22:6n-3 (DHA) |
| LANPMZ | 0.1 | 0.4 | 0.0 | 0.0 | 0.1 | 0.0 | 0.0 |
| LANPMZ | 0.7 | 0.4 | 0.1 | 0.4 | 0.7 | 0.0 | 0.1 |
| LANPMZ | 1.7 | 0.3 | 0.2 | 0.6 | 1.3 | 0.0 | 0.3 |
| LANPMZ | 3.2 | 0.3 | 0.2 | 1.0 | 2.0 | 0.0 | 0.5 |
| LANPMZ | 3.9 | 0.3 | 0.2 | 1.1 | 2.3 | 0.0 | 0.7 |
| LANPMZ | 4.7 | 0.3 | 0.2 | 1.2 | 2.5 | 0.0 | 0.9 |
| LANPMZ | 5.2 | 0.3 | 0.3 | 1.2 | 2.8 | 0.0 | 1.1 |
| LANPMZ | 5.3 | 0.3 | 0.3 | 1.4 | 2.9 | 0.0 | 1.2 |
| LANPMZ | 5.5 | 0.3 | 0.3 | 1.3 | 3.0 | 0.0 | 1.3 |
| LANPMZ | 5.6 | 0.3 | 0.3 | 1.4 | 3.0 | 0.0 | 1.3 |
| LAODDN | 0.2 | 0.4 | 0.0 | 0.0 | 0.1 | 0.0 | 0.0 |
| LAODDN | 0.4 | 0.4 | 0.0 | 0.2 | 0.3 | 0.0 | 0.0 |
| LAODDN | 1.6 | 0.3 | 0.1 | 0.4 | 1.0 | 0.0 | 0.2 |
| LAODDN | 2.4 | 0.3 | 0.2 | 0.6 | 1.4 | 0.0 | 0.3 |
| LAODDN | 3.2 | 0.3 | 0.2 | 0.8 | 1.9 | 0.0 | 0.5 |
| LAODDN | 4.0 | 0.3 | 0.3 | 0.8 | 2.3 | 0.0 | 0.7 |
| LAODDN | 4.5 | 0.3 | 0.3 | 0.9 | 2.4 | 0.0 | 0.9 |
| LAODDN | 4.6 | 0.3 | 0.3 | 1.0 | 2.6 | 0.0 | 1.0 |
| LAODDN | 4.9 | 0.3 | 0.3 | 0.9 | 2.6 | 0.0 | 1.0 |
| LAODDN | 4.5 | 0.3 | 0.3 | 0.8 | 2.5 | 0.0 | 0.9 |
| LBFGKN | 0.1 | 0.4 | 0.0 | 0.0 | 0.0 | 0.0 | 0.0 |
| LBFGKN | 0.4 | 0.4 | 0.0 | 0.2 | 0.2 | 0.0 | 0.1 |
| LBFGKN | 2.0 | 0.4 | 0.1 | 0.3 | 0.8 | 0.0 | 0.4 |
| LBFGKN | 3.2 | 0.3 | 0.1 | 0.4 | 1.2 | 0.0 | 0.5 |
| LBFGKN | 4.7 | 0.3 | 0.1 | 0.5 | 1.7 | 0.1 | 0.8 |
| LBFGKN | 6.1 | 0.3 | 0.2 | 0.6 | 2.0 | 0.1 | 1.1 |
| LBFGKN | 6.7 | 0.3 | 0.2 | 0.6 | 2.1 | 0.1 | 1.4 |
| LBFGKN | 6.8 | 0.3 | 0.2 | 0.6 | 2.1 | 0.1 | 1.4 |
| LBFGKN | 7.3 | 0.3 | 0.2 | 0.6 | 2.3 | 0.1 | 1.6 |
| LBFGKN | 7.6 | 0.3 | 0.2 | 0.6 | 2.4 | 0.0 | 1.7 |
| LBFLFK | 0.0 | 0.4 | 0.0 | 0.0 | 0.0 | 0.0 | 0.0 |
| LBFLFK | 1.0 | 0.4 | 0.1 | 0.3 | 0.4 | 0.0 | 0.2 |
| LBFLFK | 3.3 | 0.3 | 0.3 | 0.5 | 1.5 | 0.1 | 0.4 |
| LBFLFK | 4.8 | 0.3 | 0.4 | 0.6 | 2.1 | 0.2 | 0.6 |
| LBFLFK | 6.2 | 0.3 | 0.6 | 0.8 | 2.7 | 0.2 | 0.8 |
| LBFLFK | 7.5 | 0.3 | 0.5 | 0.9 | 3.1 | 0.2 | 1.0 |
| LBFLFK | 7.8 | 0.3 | 0.6 | 1.0 | 3.3 | 0.2 | 1.1 |
| LBFLFK | 8.1 | 0.3 | 0.7 | 0.9 | 3.5 | 0.2 | 1.2 |
| LBFLFK | 8.3 | 0.3 | 0.7 | 0.9 | 3.5 | 0.2 | 1.3 |
| LBFLFK | 8.6 | 0.3 | 0.7 | 0.9 | 3.6 | 0.2 | 1.4 |

Example 2. Correlation of GDD with Fatty Acid Profile

Example 1 demonstrates that EPA and DHA accumulation in transgenic canola does not follow the known pattern of PUFA accumulation in non-transgenic canola. Therefore, experimental field trials were conducted to further examine the accumulation pattern of EPA and DHA with respect to swathing time, with the goal of discovering means to optimize the production of EPA and DHA in seed oil. Experimental field trials were conducted in 2014 at six different sites, spanning four different states in USDA growth zones 4 and 6. Homozygous T3 plants of independent transgenic events LBFLFK, LBFDAU, LBFDGG, LBFGKN, LBFIHE, and LBFPRA (described in PCT/EP2015/076631) were grown in each location in replicated plots. Plants were managed according to standard agricultural practices for canola. All plants at a given location were swathed on the same date. Seeds were harvested and subjected to fatty acid profiling as described in Example 1. Accumulated GDD for each location was calculated as described in Example 1. Location level accumulated GDD and fatty acid profile data for each transgenic event is shown in Table 2. Accumulated GDD values were calculated for various developmental intervals including the time from planting to flowering, from flowering to swathing, and from planting to swathing.

TABLE 2

Accumulated GDD and fatty acid profile data for each transgenic event grown at six different field sites in the continental US in 2014. GDD41 refers to accumulated GDD calculated using T-base value of 41 degrees F.. The content fatty acids is expressed as percentage (weight of a particular fatty acid) of the (total weight of all fatty acids).

| Event | Location | GDD41 Planting to Flowering | GDD41 First Flower to Swathing | GDD41 Planting to Swathing | EPA + DHA | EPA (20:5n-3) | ARA (20:4n-6) | DHA (22:6n-3) | DPA (22:5n-3) | 18:1n-9 |
|---|---|---|---|---|---|---|---|---|---|---|
| LBFLFK | 1 | 1112 | 1344 | 2430 | 7.7 | 6.7 | 1.6 | 1.0 | 2.6 | 32.4 |
| LBFLFK | 2 | 1398 | 1694 | 3064 | 9.6 | 8.4 | 1.8 | 1.3 | 3.3 | 30.8 |
| LBFLFK | 3 | 1097 | 1791 | 2864 | 9.2 | 7.9 | 1.9 | 1.3 | 3.1 | 29.4 |
| LBFLFK | 4 | 979 | 1528 | 2486 | 9.4 | 8.2 | 2.2 | 1.2 | 3.0 | 31.8 |
| LBFLFK | 5 | 1037 | 1778 | 2799 | 10.2 | 8.7 | 2.0 | 1.5 | 3.6 | 28.0 |
| LBFLFK | 6 | 1009 | 1704 | 2692 | 10.9 | 9.3 | 2.2 | 1.6 | 3.5 | 29.4 |
| LBFDAU | 1 | 1112 | 1344 | 2430 | 10.9 | 9.4 | 1.7 | 1.5 | 2.5 | 29.4 |
| LBFDAU | 2 | 1398 | 1694 | 3064 | 11.9 | 10.5 | 1.7 | 1.4 | 2.7 | 30.1 |
| LBFDAU | 3 | 1097 | 1791 | 2864 | 12.5 | 10.8 | 2.2 | 1.7 | 3.0 | 27.9 |
| LBFDAU | 4 | 979 | 1528 | 2486 | 12.8 | 11.2 | 2.3 | 1.6 | 2.6 | 31.3 |
| LBFDAU | 5 | 1037 | 1778 | 2799 | 13.8 | 11.8 | 2.1 | 2.0 | 3.2 | 26.2 |
| LBFDAU | 6 | 1009 | 1704 | 2692 | 11.8 | 10.2 | 2.2 | 1.5 | 2.6 | 29.5 |
| LBFDGG | 1 | 1112 | 1344 | 2430 | 6.0 | 5.1 | 1.6 | 0.9 | 1.8 | 36.0 |
| LBFDGG | 2 | 1398 | 1694 | 3064 | 7.0 | 6.1 | 1.7 | 0.9 | 2.2 | 35.2 |
| LBFDGG | 3 | 1097 | 1791 | 2864 | 7.1 | 5.9 | 1.9 | 1.2 | 2.2 | 32.8 |
| LBFDGG | 4 | 979 | 1528 | 2486 | 7.2 | 6.2 | 2.1 | 1.0 | 2.0 | 35.7 |
| LBFDGG | 5 | 1037 | 1778 | 2799 | 7.2 | 6.2 | 1.8 | 1.1 | 2.2 | 33.0 |
| LBFDGG | 6 | 1009 | 1704 | 2692 | 7.1 | 6.0 | 2.0 | 1.1 | 2.0 | 35.2 |
| LBFGKN | 1 | 1112 | 1344 | 2430 | 6.0 | 5.0 | 1.6 | 0.9 | 1.7 | 35.2 |
| LBFGKN | 2 | 1398 | 1694 | 3064 | 7.6 | 6.6 | 1.9 | 1.0 | 2.1 | 33.4 |
| LBFGKN | 3 | 1097 | 1791 | 2864 | 6.8 | 5.7 | 1.9 | 1.1 | 2.0 | 33.4 |
| LBFGKN | 4 | 979 | 1528 | 2486 | 6.8 | 5.8 | 2.0 | 0.9 | 1.9 | 35.7 |
| LBFGKN | 5 | 1037 | 1778 | 2799 | 7.8 | 6.5 | 1.8 | 1.2 | 2.2 | 31.7 |
| LBFGKN | 6 | 1009 | 1704 | 2692 | 7.1 | 6.0 | 2.0 | 1.1 | 2.0 | 34.1 |
| LBFIHE | 1 | 1112 | 1344 | 2430 | 7.3 | 6.2 | 2.2 | 1.1 | 1.8 | 32.2 |
| LBFIHE | 2 | 1398 | 1694 | 3064 | 7.4 | 6.3 | 1.8 | 1.1 | 2.0 | 32.4 |
| LBFIHE | 3 | 1097 | 1791 | 2864 | 8.1 | 6.8 | 2.6 | 1.3 | 2.0 | 30.7 |
| LBFIHE | 4 | 979 | 1528 | 2486 | 7.9 | 6.8 | 2.5 | 1.1 | 1.9 | 32.3 |
| LBFIHE | 5 | 1037 | 1778 | 2799 | 7.1 | 6.0 | 2.1 | 1.0 | 1.8 | 32.0 |
| LBFIHE | 6 | 1009 | 1704 | 2692 | 8.0 | 6.8 | 2.6 | 1.2 | 1.9 | 31.1 |
| LBFPRA | 1 | 1112 | 1344 | 2430 | 9.2 | 8.3 | 3.2 | 0.9 | 2.0 | 30.3 |
| LBFPRA | 2 | 1398 | 1694 | 3064 | 10.1 | 9.1 | 3.2 | 1.0 | 2.4 | 30.9 |
| LBFPRA | 3 | 1097 | 1791 | 2864 | 10.4 | 9.3 | 3.7 | 1.1 | 2.3 | 28.0 |
| LBFPRA | 4 | 979 | 1528 | 2486 | 11.0 | 10.0 | 4.3 | 1.0 | 2.2 | 28.9 |
| LBFPRA | 5 | 1037 | 1778 | 2799 | 11.4 | 10.1 | 4.0 | 1.2 | 2.7 | 25.9 |
| LBFPRA | 6 | 1009 | 1704 | 2692 | 11.5 | 10.3 | 4.1 | 1.2 | 2.5 | 27.5 |

The accumulation of GDD at each location was distinct and allowed for a correlation analysis to be performed between the fatty acid profile and the accumulated GDD. Pearson correlation coefficients of various parameters are presented in Table 3. For each event, the highest correlation coefficient value for EPA+DHA is with GDD41 First Flower to Swathing (italicized cells in Table 3). This observation is also true for EPA and DHA individually, as well as for DPA. Therefore, in 2014 the accumulated GDD from flowering to swathing is the best indicator of EPA, DHA, and DPA accumulation in seed oil.

TABLE 3

Pearson correlation coefficients (R value) between accumulated GDD41 and fatty acid content in mature canola seeds from six different transgenic events grown at various locations in 2014.

| GDD | Event | EPA + DHA | EPA (20:5n-3) | ARA (20:4n-6) | DHA (22:6n-3) | DPA (22:5n-3) | 18:1n-9 |
|---|---|---|---|---|---|---|---|
| GDD41 Planting to First Flower | LBFDAU | -0.32 | -0.26 | -0.76 | -0.45 | -0.11 | 0.15 |
| | LBFDGG | -0.12 | -0.04 | -0.64 | -0.39 | 0.27 | 0.11 |
| | LBFGKN | 0.29 | 0.36 | -0.25 | -0.15 | 0.14 | -0.20 |
| | LBFIHE | -0.32 | -0.31 | -0.78 | -0.32 | 0.32 | 0.33 |
| | LBFLFK | -0.16 | -0.14 | -0.52 | -0.26 | -0.04 | 0.16 |
| | LBFPRA | -0.51 | -0.51 | -0.80 | -0.49 | -0.06 | 0.67 |
| GDD41 First Flower to Swathing | LBFDAU | 0.62 | 0.62 | 0.41 | 0.49 | 0.79 | -0.55 |
| | LBFDGG | 0.81 | 0.74 | 0.32 | 0.80 | 0.94 | -0.79 |
| | LBFGKN | 0.80 | 0.74 | 0.52 | 0.81 | 0.93 | -0.79 |
| | LBFIHE | 0.20 | 0.17 | 0.01 | 0.30 | 0.54 | -0.53 |
| | LBFLFK | 0.76 | 0.72 | 0.39 | 0.82 | 0.87 | -0.89 |
| | LBFPRA | 0.63 | 0.60 | 0.27 | 0.71 | 0.82 | -0.60 |

TABLE 3-continued

Pearson correlation coefficients (R value) between accumulated GDD41 and fatty acid content in mature canola seeds from six different transgenic events grown at various locations in 2014.

| GDD | Event | EPA + DHA | EPA (20:5n-3) | ARA (20:4n-6) | DHA (22:6n-3) | DPA (22:5n-3) | 18:1n-9 |
|---|---|---|---|---|---|---|---|
| GDD41 | LBFDAU | 0.26 | 0.29 | −0.17 | 0.09 | 0.51 | −0.31 |
| Planting | LBFDGG | 0.52 | 0.51 | −0.16 | 0.34 | 0.85 | −0.51 |
| to | LBFGKN | 0.77 | 0.77 | 0.22 | 0.50 | 0.77 | −0.70 |
| Swathing | LBFIHE | −0.06 | −0.08 | −0.48 | 0.01 | 0.59 | −0.18 |
| | LBFLFK | 0.45 | 0.45 | −0.04 | 0.43 | 0.62 | −0.55 |
| | LBFPRA | 0.14 | 0.12 | −0.30 | 0.22 | 0.57 | −0.02 |

Experimental field trials were conducted in 2015 at six different sites, spanning four different states in USDA growth zone 4. Homozygous T4 plants of events LBFDAU and LBFLFK were grown in each location in replicated plots. Plants were managed according to standard agricultural practices for canola. All plants at a given location were swathed on the same date. Seeds were harvested and subjected to fatty acid profiling as described in Example 1. Accumulated GDD for each location was calculated as described in Example 1. Location level accumulated GDD and fatty acid profile data for each transgenic event grown in 2015 is shown in Table 4. Accumulated GDD values were calculated for the same developmental intervals as in 2014.

TABLE 4

Accumulated GDD and fatty acid profile data for each transgenic event grown at six different field sites in the continental US in 2015. GDD41 refers to accumulated GDD calculated using T-base value of 41 degrees F.. The content of fatty acids is expressed as percentage (weight of a particular fatty acid) of the (total weight of all fatty acids).

| Event | Location | GDD41 Planting to Flowering | GDD41 First Flower to Swathing | GDD41 Planting to Swathing | EPA + DHA | EPA (20:5n-3) | ARA (20:4n-6) | DHA (22:6n-3) | DPA (22:5n-3) | 18:1n-9 |
|---|---|---|---|---|---|---|---|---|---|---|
| LBFDAU | 1 | 800 | 1539 | 2325 | 10.38 | 8.89 | 2.12 | 1.48 | 2.80 | 27.33 |
| LBFDAU | 2 | 1157 | 1246 | 2380 | 11.30 | 9.96 | 2.81 | 1.34 | 2.68 | 28.74 |
| LBFDAU | 3 | 1096 | 1387 | 2473 | 10.02 | 8.84 | 2.04 | 1.17 | 2.79 | 30.67 |
| LBFDAU | 4 | 1173 | 1171 | 2319 | 8.73 | 7.59 | 2.25 | 1.14 | 2.15 | 30.17 |
| LBFDAU | 5 | 1181 | 1200 | 2361 | 10.83 | 9.40 | 2.84 | 1.43 | 2.84 | 27.29 |
| LBFDAU | 6 | 962 | 1423 | 2361 | 10.64 | 9.24 | 3.07 | 1.40 | 2.42 | 30.20 |
| LBFLFK | 1 | 800 | 1539 | 2325 | 6.76 | 6.09 | 1.86 | 0.68 | 3.12 | 28.62 |
| LBFLFK | 2 | 1157 | 1246 | 2380 | 7.19 | 6.54 | 2.59 | 0.66 | 3.01 | 31.29 |
| LBFLFK | 3 | 1096 | 1387 | 2473 | 6.64 | 6.07 | 1.75 | 0.57 | 3.15 | 32.23 |
| LBFLFK | 4 | 1173 | 1171 | 2319 | 6.80 | 6.15 | 2.36 | 0.65 | 2.97 | 32.08 |
| LBFLFK | 5 | 1181 | 1200 | 2361 | 7.00 | 6.33 | 2.42 | 0.67 | 3.09 | 29.63 |
| LBFLFK | 6 | 962 | 1423 | 2361 | 8.44 | 7.51 | 3.32 | 0.93 | 3.16 | 30.89 |

The accumulation of GDD at each location was distinct and allowed for a correlation analysis to be performed between the fatty acid profile and the accumulated GDD. Pearson correlation coefficients of various parameters are presented in Table 5. Again, the highest positive correlation values for EPA and DHA were with GDD41 from flowering to swathing. The strength of the correlation in 2015 was not as high as in 2014, but the trend was similar. Environmental factors that are not part of the GDD calculation, such as rainfall, humidity, and field location, may be the reason why the correlation is not as strong in 2015 compared to 2014.

TABLE 5

Pearson correlation coefficients (R value) between accumulated GDD41 and fatty acid content in mature canola seeds from six different transgenic events grown at various locations in 2015.

| GDD | Event | EPA + DHA | EPA (20:5n-3) | ARA (20:4n-6) | DHA (22:6n-3) | DPA (22:5n-3) | 18:1n-9 |
|---|---|---|---|---|---|---|---|
| GDD41 Planting to First Flower | LBFDAU | −0.12 | −0.03 | 0.21 | −0.56 | −0.20 | 0.24 |
| | LBFLFK | −0.19 | −0.15 | 0.10 | −0.37 | −0.59 | 0.61 |
| GDD41 First Flower to Swathing | LBFDAU | 0.20 | 0.14 | −0.26 | 0.44 | 0.35 | −0.08 |
| | LBFLFK | 0.17 | 0.14 | −0.19 | 0.28 | 0.76 | −0.45 |
| GDD41 Planting to Swathing | LBFDAU | 0.20 | 0.29 | −0.19 | −0.38 | 0.45 | 0.45 |
| | LBFLFK | −0.15 | −0.10 | −0.30 | −0.36 | 0.44 | 0.49 |

Figure 2:
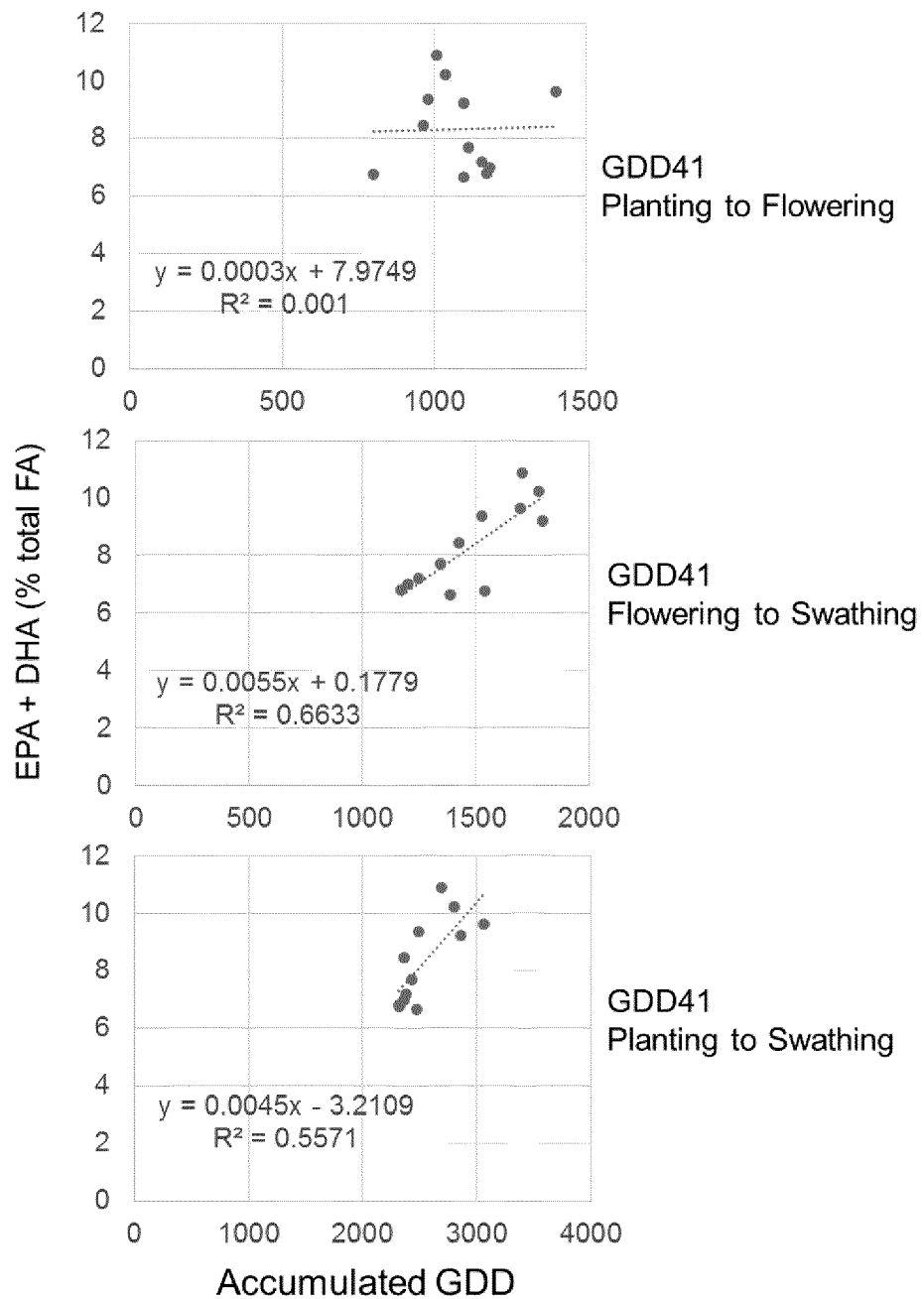
FIG. 2: Plots of EPA+DHA content vs accumulated GDD41 for various developmental periods. Data from event LBFLFK from 2014 and 2015 are included. Each data point represents average data for a single location in a single year. GDD41 refers to accumulated GDD calculated using T-base value of 41 degrees F. The content of fatty acids is expressed as percentage (weight of a particular fatty acid) of the (total weight of all fatty acids).
Figure 3:
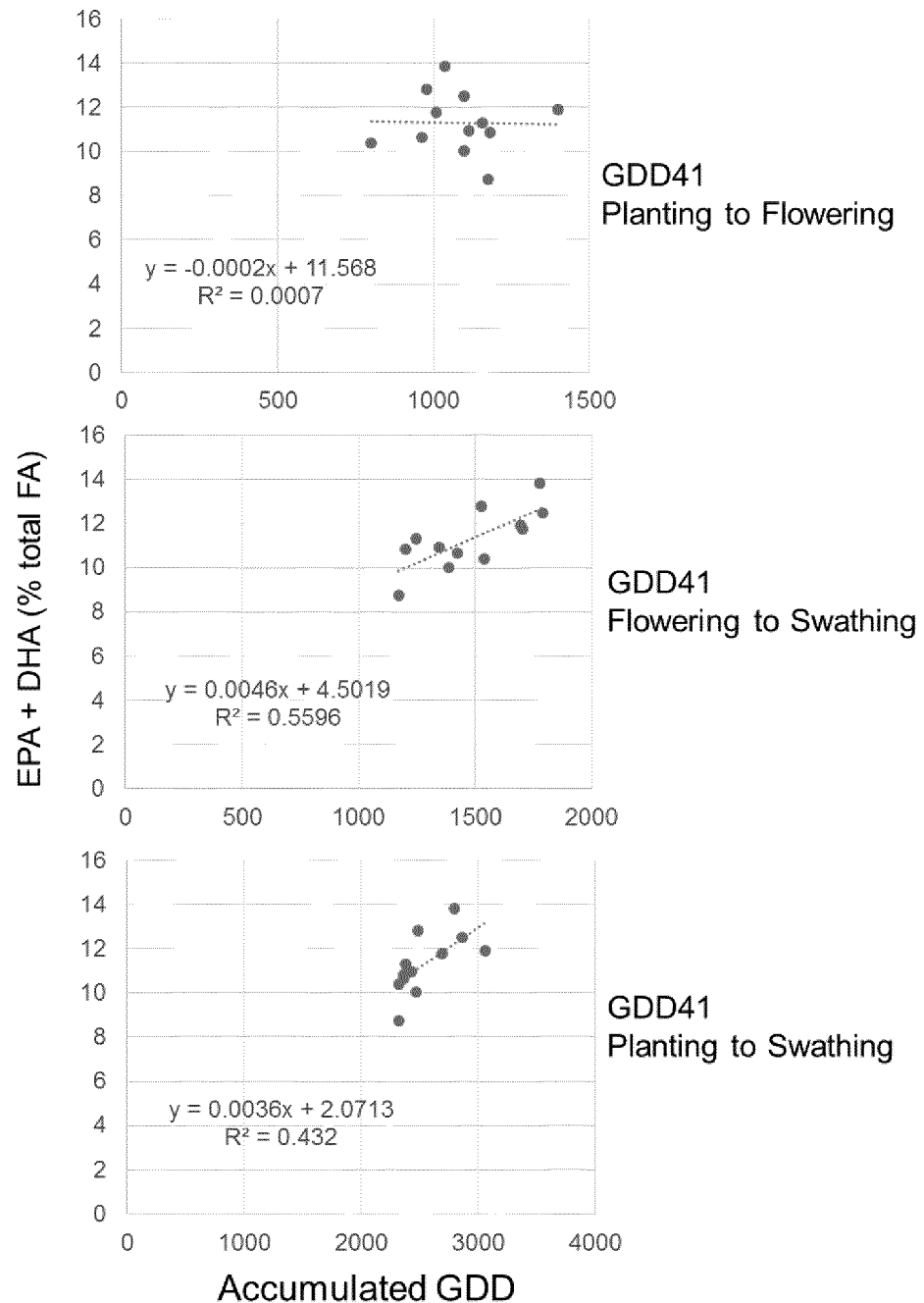
FIG. 3: Plots of EPA+DHA content vs accumulated GDD41 for various developmental periods. Data from event LBFDAU from 2014 and 2015 are included. Each data point represents average data for a single location in a single year. GDD41 refers to accumulated GDD calculated using T-base value of 41 degrees F. The content of fatty acids is expressed as percentage (weight of a particular fatty acid) of the (total weight of all fatty acids).
Figure 4:
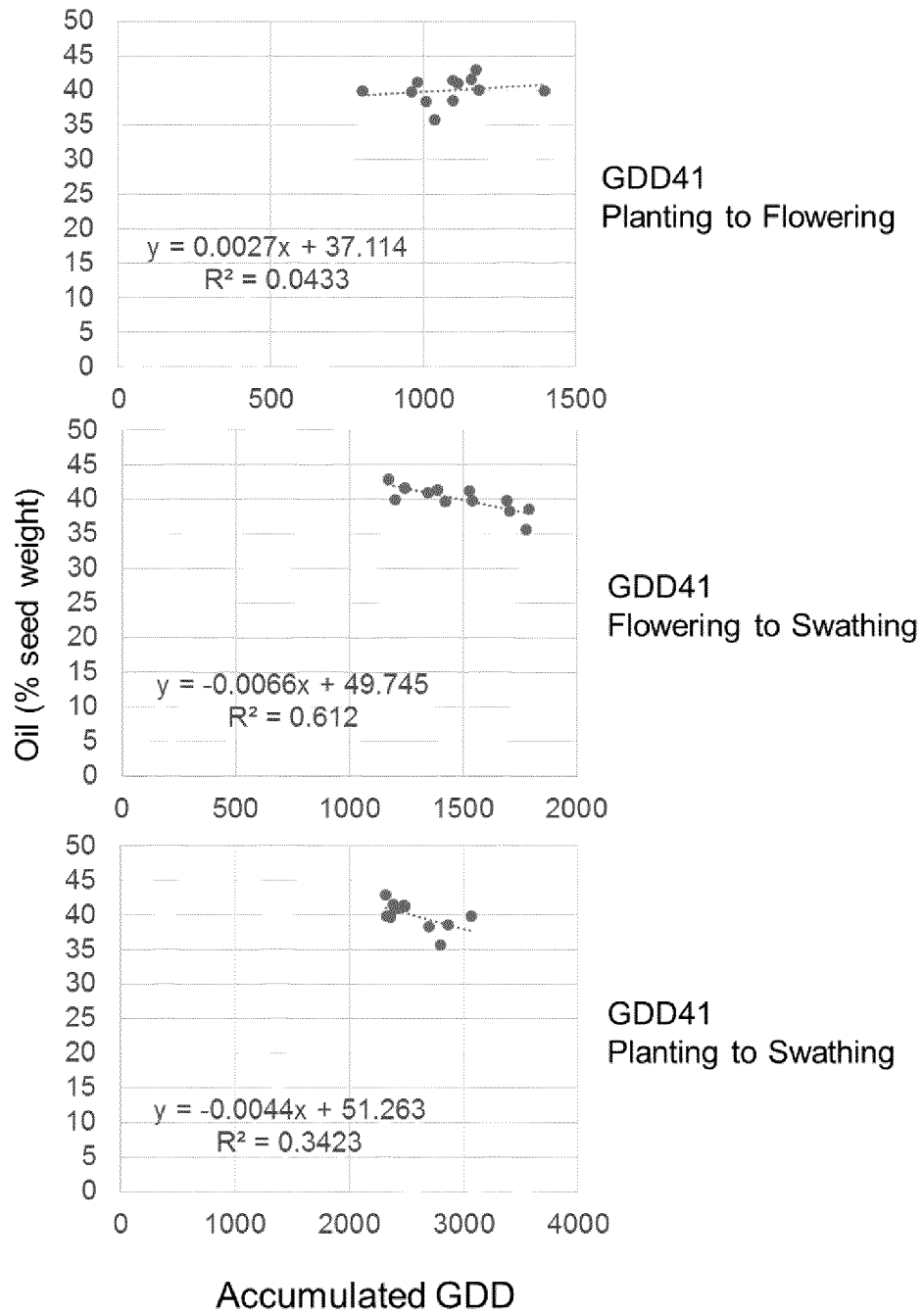
FIG. 4: Plots of Oil content vs accumulated GDD41 for various developmental periods. Data from event LBFLFK from 2014 and 2015 are included. Each data point represents average data for a single location in a single year. GDD41 refers to accumulated GDD calculated using T-base value of 41 degrees F. The content of oil is expressed as percentage (weight of oil) of the total seed weight.
Figure 5:
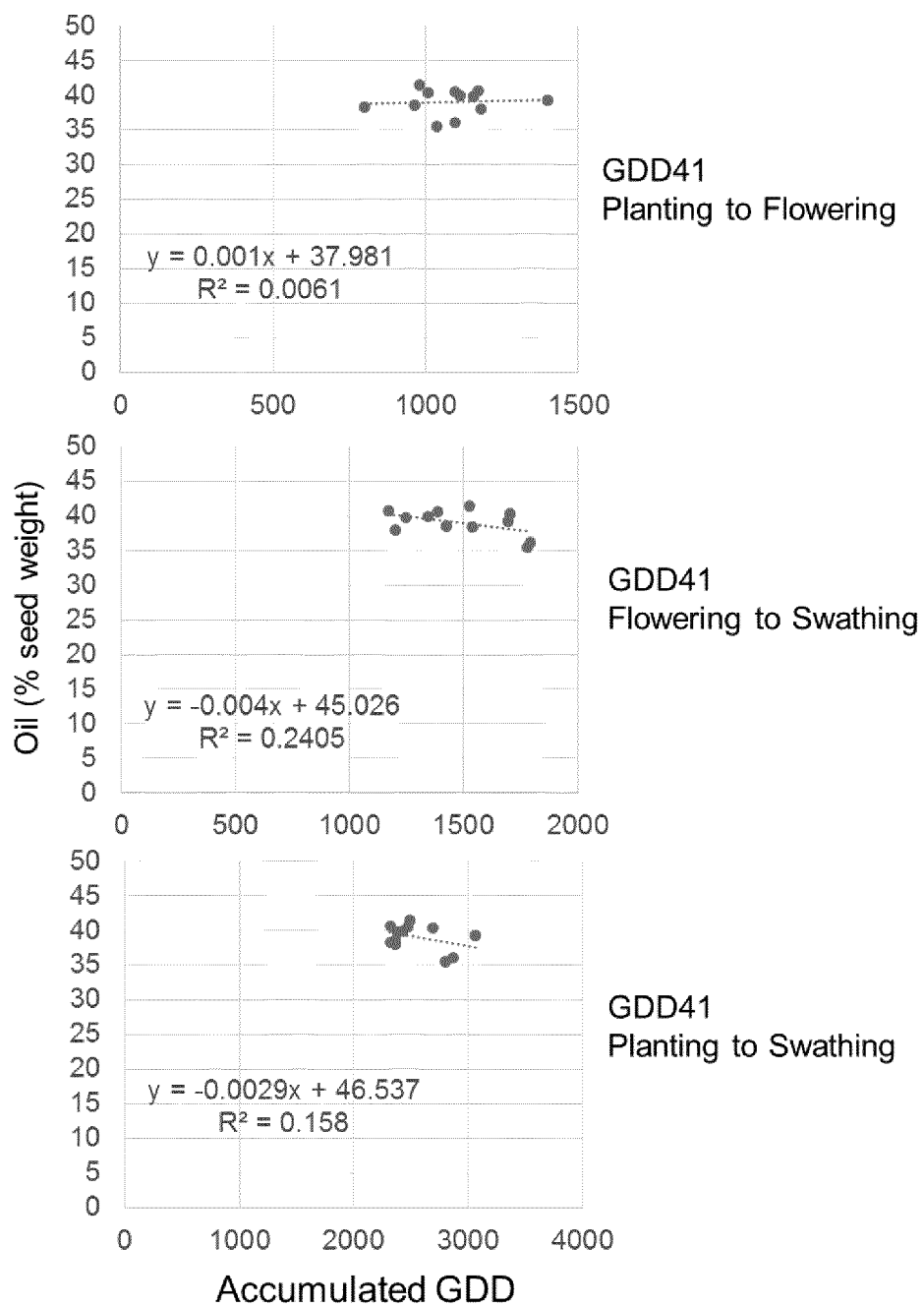
FIG. 5: Plots of Oil content vs accumulated GDD41 for various developmental periods. Data from event LBFDAU from 2014 and 2015 are included. Each data point represents average data for a single location in a single year. GDD41 refers to accumulated GDD calculated using T-base value of 41 degrees F. The content of oil is expressed as percentage (weight of oil) of the total seed weight.

An across-year analysis was performed combining the data from 2014 and 2015 for events LBFLFK and LBFDAU. FIG. 2 shows plots of EPA+DHA content in seed oil vs accumulated GDD values for various developmental intervals for event LBFLFK and FIG. 3 shows the corresponding plots for event LBFDAU. For each event and for each developmental interval a correlation was calculated between EPA+DHA and GDD, and the resulting R2 values are shown on the plots. For both LBFLFK and LBFDAU the highest R2 value is for EPA+DHA vs GDD41 from flowering to swathing. This means that the accumulated GDD from flowering to swathing is the best indicator of EPA+DHA content in seeds and may be useful as a predictor. FIGS. 4 and 5 show plots of oil content vs accumulated GDD for various developmental intervals for events LBFLFK and LBFDAU, respectively. For both events oil content is most highly correlated with the accumulated GDD from flowering to swathing. The correlation is negative in both cases, meaning that higher accumulated GDD correlates with lower oil content. The influence of temperature during seed development has been studied in crop plants (e.g. Deng and Scarth 1998 JAOCS 75:759-766, Schulte et al. 2013 Industrial Crops and Products 51:212-219, Vera et al. 2007 Canadian J. Plant Sci 87:13-26). For canola, 18:1n-9 content increases during seed development reaching a maximum in mature seed, and reaching a higher maximum when temperatures are relatively high during seed development. Similar observations were made for camelina and soybean seeds. Together, these results suggest that in oil seed crops a higher GDD would result in higher 18:1n-9 content. 18:1n-9 is the precursor for the synthesis of EPA and DHA, and based on the literature one may predict that EPA and DHA content as a proportion of total fatty acids would decline with higher GDD accumulation. On the contrary, we discovered that EPA and DHA content tends to reach a higher concentration in seeds that have accumulated the most GDD from flowering to swathing, as shown in FIGS. 2 and 3. A grower may use this information to maximize EPA+DHA content in field grown plants, for example, by swathing plants only after the accumulated GDD41 from flowering has reached at least 1600 units. The impact of such a cutoff can be evaluated by applying it to the 2014 and 2015 field data presented in this example. The average EPA+DHA content of seed oil from all 2014 and 2015 field sites for event LBFLFK is 8.29%. Selecting sites where GDD41 from flowering to swathing was greater than 1600 units gives an EPA+DHA concentration of 9.99%, which is a relative increase of 20.5%. Applying the same criteria to event LBFDAU would result in an EPA+DHA content of 12.49%, compared to 11.3% from all field sites. This is a relative increase in EPA+DHA content of 10.6%.

In practice, a grower may achieve a desired number of GDD units in several ways. A planting date may be chosen to increase the likelihood of achieving a desired GDD from flowering to swathing. Once the first flowers are present in the field, the GDD can be actively monitored and swathing can be done only once the GDD has reached the desired value. The transgenic event may also be bred into germplasm with differing flowering dates or maturity times such that at least 1600 accumulated GDD41 from flowering to swathing can be achieved in any given location. Most likely, a combination of approaches would be taken to achieve the desired GDD from flowering to swathing in order to maximize EPA+DHA content.

Example 3. Analysis of Correlation of GDD with EPA and DHA Content Over Multiple Generations Five seed lots of EPA+DHA canola event LBFLFK (event described in PCT/EP2015/076631) representing three different generations (T3-T5) and two different production environments (greenhouse vs field) were grown in a single field in Hawaii. Seeds were sown in late December 2015. A weather station was deployed at the edge of the field to record atmospheric data. Flowering racemes were marked and immature seed samples were harvested at 25 days after flowering (DAF) and 35 DAF as described in Example 1. All immature seed samples were collected and pooled from 12-14 different plants per seed lot. Seed samples were also collected at maturity and at late maturity. Maturity was defined as the BBCH 86 stage, when 60% of pods are ripe with dark, hard seeds. Late maturity is defined as 2 weeks after maturity. At maturity, four different types of samples were harvested from plants of each seed lot:
1) Seeds the lower portion of the main raceme
2) Seeds from the upper portion of the main raceme
3) All pods from the main raceme
4) All pods from the branches Each sampling consisted of pooling pods from 12-14 individual plants per entry. Sample types 1 and 2 were collected from the same plants for each seed lot. Sample types 3 and 4 were collected from the same plants for each seed lot. All immature, mature, and late mature seed samples were subject to GC-FID for determination of fatty acid composition, as described in Example 1. The mature and late mature samples were subject to Near Infrared Spectroscopy (NIRS) to determine the approximate oil content of the seeds.

Figure 6:
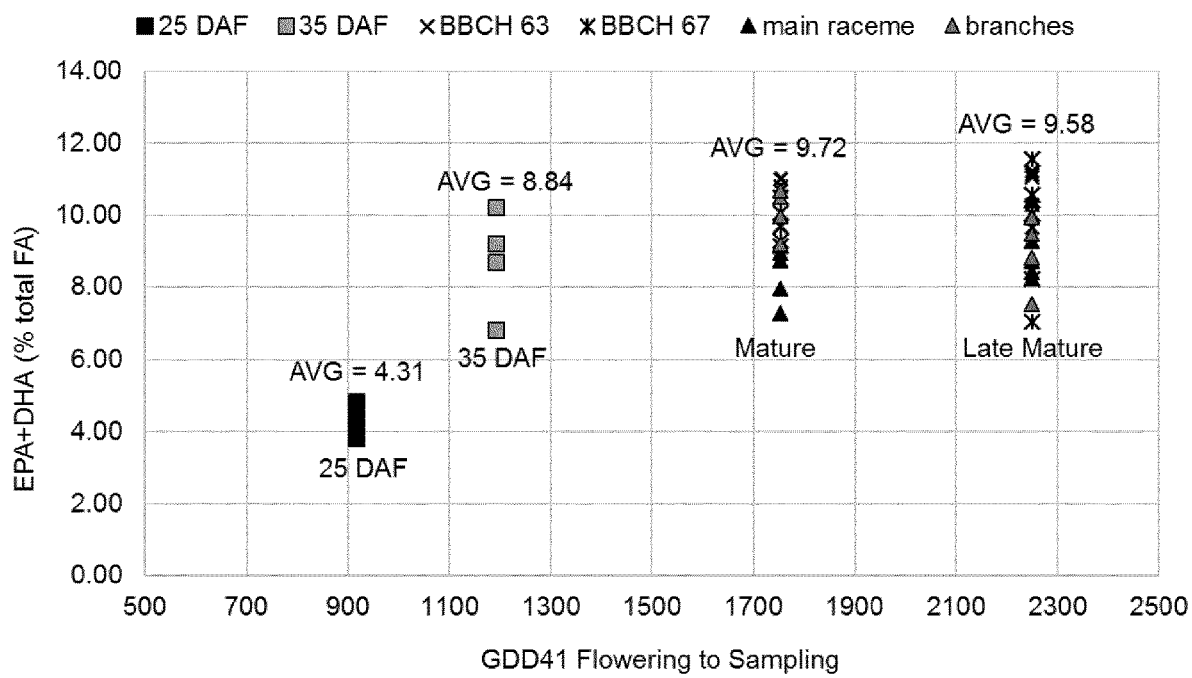
FIG. 6: EPA+DHA accumulation during the course of seed development. EPA+DHA data shown is the mean of all technical replicates. GDD41 is the accumulated growing degree days calculated based on a T-base of 41° F. 25 DAF and 35 DAF refers to the immature samples. BBCH63 refers to samples taken from the lower portion of the main raceme and BBCH67 refers to samples taken from the upper portion of the main raceme.
Figure 7:
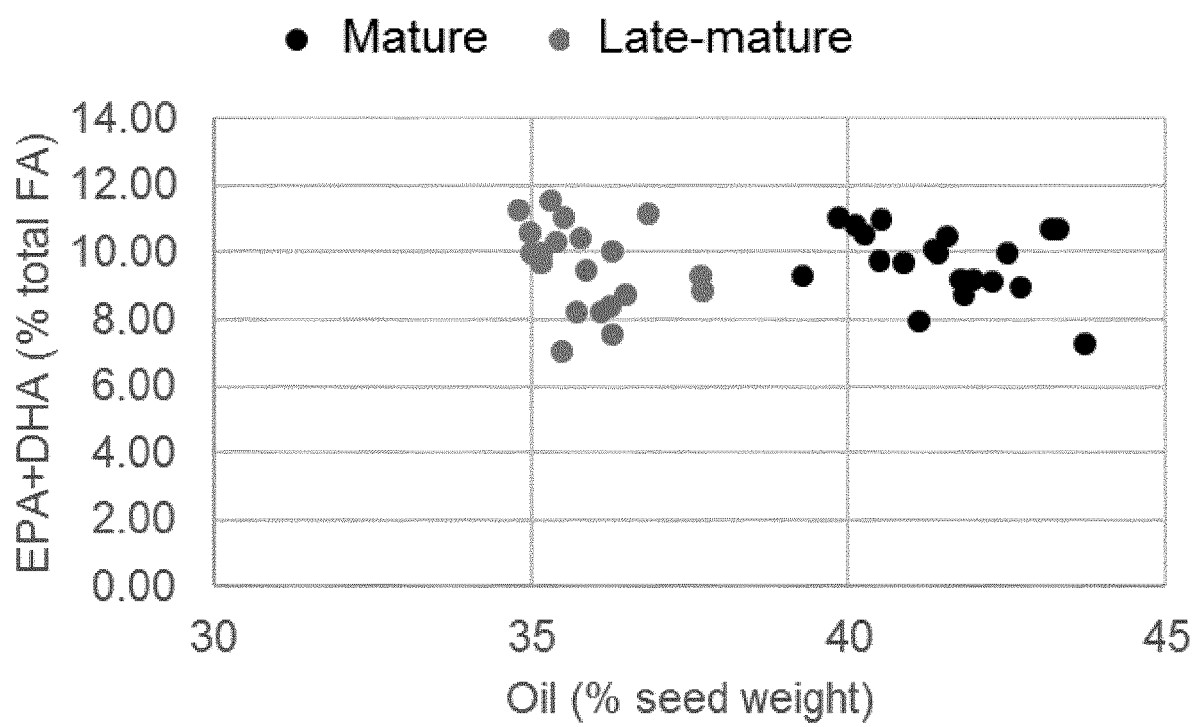
FIG. 7: EPA+DHA and Oil content in mature and late mature seed samples.

The temperature data was used to calculate growing degree days (GDDs) as described in Example 1, using T-base of 41 degrees F. FIG. 6 is a plot of EPA+DHA content in all samples as a function of GDD accumulation from the onset of flowering to the time of sample collection. The figure shows that EPA+DHA content increases as seeds mature. EPA+DHA accumulates at a high rate during the middle of seed development, doubling from 25 DAF to 35 DAF. From 35 DAF to maturity, EPA+DHA increases slightly and then does not change between maturity and late-maturity. This data shows that EPA+DHA content can be maximized by insuring that the seed have reached full maturity prior to harvest. It is therefore recommended to use GDD, particularly GDD accumulation from the onset of flowering to swathing/harvest, to estimate seed maturity. In this experiment, we confirmed the findings in Example 2 that a GDD of at least 1600 units correlated with seed maturity and maximum EPA+DHA content. The percentage of EPA+DHA in seed oil does not decrease from maturity to late maturity (FIG. 6). There were no patterns in EPA+DHA content that correlated with source seed production environment. There was also not a consistent increase or decrease in EPA+DHA content when progressing from one generation to the next, even when looking at three generations where the source seeds were produced in the same greenhouse environment. Therefore, the EPA+DHA production trait appears to be stable over at least three generations of EPA+DHA canola event LBFLFK. The degree of seed maturity, defined by days after flowering or by GDD accumulation, does appear to correlate strongly with EPA+DHA content. However, total oil content does decrease from maturity to late-maturity (FIG. 7), which is known phenomenon for most oil seeds, including canola. Therefore, to maximize EPA+DHA yield per acre, it is critical to harvest seeds not until EPA+DHA reaches a maximum, but before total oil content begins to decline.

The invention claimed is:

1. A method for the commercial production of oil enriched with a very long chain polyunsaturated fatty acid (VLCPUFA) from seeds of a transgenic *Brassica napus* variety capable of producing said VLCPUFA, which method comprises:
   (i) calculating the accumulated Growing Degree Days (GDD) in ° F., starting from the appearance of the first open flower, wherein the GDD is calculated with a TBase of 41° F.,
   (ii) swathing the plants when the accumulated GDD reaches a value of at least 1600, and
   (iii) harvesting seeds from the swathed plants of (ii), and processing the seeds to produce oil enriched in said VLCPUFA.

2. The method of claim 1, wherein the VLCPUFA comprises eicosapentaenoic acid (EPA) and/or docosahexaenoic acid (DHA).

3. The method of claim 1, wherein the plants are swathed when the accumulated GDD is from 1600 to 2200 GDD.

4. The method of claim 2, wherein the plants are swathed when the accumulated GDD is from 1600 to 2200 GDD.

5. The method of claim 1, wherein seed from said plant has an oil content of 20% to 55%.

6. The method of claim 2, wherein seed from said plant has an oil content of 20% to 55%.

7. The method of claim 4, wherein seed from said plant has an oil content of 20% to 55%.

8. The method of claim 2, wherein the oil has a combined EPA and DHA content of between 4% and 25%.

9. The method of claim 4, wherein the oil has a combined EPA and DHA content of between 4% and 25%.

10. The method of claim 6, wherein the oil has a combined EPA and DHA content of between 4% and 25%.

11. The method of claim 1, wherein the seeds are harvested before late maturity.

* * * * *